United States Patent [19]

Sunagawa et al.

[11] Patent Number: 5,112,966

[45] Date of Patent: May 12, 1992

[54] BETA-LACTAMS

[75] Inventors: Makoto Sunagawa, Toyonaka; Haruki Matsumura, Nara; Tsuneo Yano, Toyonaka; Akira Sasaki, Ibaraki; Shinzi Takata, Nishinomiya, all of Japan

[73] Assignee: Sumitomo Pharmaceuticals Company, Limited, Osaka, Japan

[21] Appl. No.: 793,290

[22] Filed: Oct. 31, 1985

[30] Foreign Application Priority Data

Oct. 31, 1984 [JP] Japan ................. 59-230790
Jan. 18, 1985 [JP] Japan ................... 60-5912

[51] Int. Cl.$^5$ .......................................... C07D 205/08
[52] U.S. Cl. ........................... 540/200; 540/300; 540/301; 540/362
[58] Field of Search ............... 540/200, 300, 301, 362

[56] References Cited

U.S. PATENT DOCUMENTS

| 4,234,596 | 11/1980 | Christensen et al. | 540/200 X |
| 4,536,334 | 8/1985 | Sunagawa et al. | 540/200 |
| 4,595,750 | 6/1986 | Christensen et al. | 540/300 |
| 4,617,152 | 10/1986 | Christensen et al. | 540/200 |
| 4,734,497 | 3/1988 | Christensen et al. | 540/200 |

FOREIGN PATENT DOCUMENTS

| 0018594 | 11/1980 | European Pat. Off. |
| 0071908 | 2/1983 | European Pat. Off. |
| 0113101 | 7/1984 | European Pat. Off. |
| 0188816 | 7/1986 | European Pat. Off. |
| 224059 | 6/1987 | European Pat. Off. |
| 230792 | 8/1987 | European Pat. Off. |
| 45559 | 3/1985 | Japan. |
| 74048 | 7/1987 | Japan. |

OTHER PUBLICATIONS

Smith, David H. et al., Heterocycles, 21, pp. 29-40 (1984).

Primary Examiner—Richard L. Raymond
Attorney, Agent, or Firm—Birch, Stewart, Kolasch & Birch

[57] ABSTRACT

A beta-lactam compound of the formula:

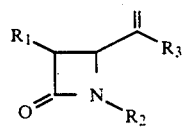

wherein $R_1$ is a hydrogen atom, a lower alkyl group or a 1-hydroxy(lower)alkyl group wherein the hydroxyl group is optionally protected, $R_2$ is a hydrogen atom or a protective group for the nitrogen atom and $R_3$ is a methyl group, a halomethyl group, a hydroxymethyl group, a protected hydroxymethyl group, a formyl group, a carboxyl group, a lower alkoxycarbonyl group or an ar(lower)alkoxycarbonyl group wherein the aryl group is optionally substituted, or $R_2$ and $R_3$ are combined together to form an oxaalkylene group and, when taken together with one nitrogen atom and two carbon atoms adjacent thereto, they represent a six-membered cyclic aminoacetal group, which is useful as a valuable intermediate in the stereospecific production of 1-methylcarbapenem compounds.

1 Claim, No Drawings

BETA-LACTAMS

This invention relates to beta-lactams and their production. More particularly, it relates to novel betalactam compounds of the formula:

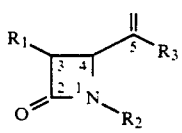
(I)

wherein $R_1$ is a hydrogen atom, a lower alkyl group or a 1-hydroxy(lower)alkyl group wherein the hydroxyl group is optionally protected, $R_2$ is a hydrogen atom or a protective group for the nitrogen atom (i.e. a nitrogen-protecting group) and $R_3$ is a methyl group, a halomethyl group, a hydroxymethyl group, a protected hydroxymethyl group, a formyl group, a carboxyl group, a lower alkoxycarbonyl group or an ar(lower)alkoxycarbonyl group wherein the aryl group is optionally substituted, or $R_2$ and $R_3$ are combined together to form an oxaalkylene group and, when taken together with one nitrogen atom and two carbon atoms adjacent thereto, they represent a six-membered cyclic aminoacetal group, and their production.

Since the successful isolation of antimicrobial "thienamycin" from nature [U.S. Pat. No. 3,950,357; J.Am.Chem.Soc., 100, 313 (1978)], various carbapenem compounds have been reported. Among them, there are known some carbapenem compounds substituted at the 1-position, and 1-methylcarbapenem compounds are particularly notable in exerting strong antimicrobial activity against various microorganisms with excellent stability in living bodies [EP-0071908A; Heterocycles, 21, 29 (984)]. However, their synthetic methods as heretofore reported are troublesome in requiring a lengthy series of reaction steps. Further, those methods are defective in that the stereospecific formation of the 1-methyl group is not possible.

As a result of the extensive study, it has now been found that the beta-lactam compounds (I) according to the invention are valuable intermediates for the production of 1-methylcarbapenem compounds having the following fundamental skeleton:

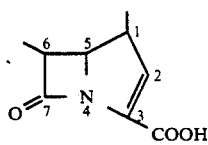

, particularly in making it possible to form the 1-methyl group stereospecifically. This invention is based on the above finding.

In the present specification, the term "lower" is intended to mean a group having not more than about 8 carbon atoms, preferably not more than about 4 carbon atoms. Examples of the lower alkyl group are methyl, ethyl, n-propyl, isopropyl, n-butyl, sec-butyl, etc. Among them, methyl and ethyl are the most preferable. Likewise, the alkyl moiety in the 1-hydroxy(lower)alkyl group may be alkyl having not more than about 8 carbon atoms, preferably not more than about 4 carbon atoms. Preferred examples of the 1-hydroxy(lower)alkyl group are hydroxymethyl, 1-hydroxyethyl, etc. The nitrogen-protecting group may be any one which can be conventionally employed for protection of the nitrogen atom in an amide group (—CONH—), and its examples are tri(lower)alkylsilyl such as tri($C_1$-$C_4$)alkylsilyl (e.g. trimethylsilyl, t-butyldimethylsilyl), substituted phenyl such as phenyl substituted with $C_1$-$C_4$ alkoxy (e.g. p-methoxyphenyl, 2,4-dimethoxyphenyl), optionally substituted mono or diarylmethyl such as mono or diphenylmethyl optionally substituted with $C_1$-$C_4$ alkoxy, $C_1$-$C_4$ alkyl, nitro, halogen, etc. on the phenyl group(s) (e.g. benzyl, p-methoxybenzyl, 2,4-dimethoxybenzyl, diphenylmethyl, di-p-anisylmethyl), substituted methyl such as methyl substituted with $C_1$-$C_4$ alkoxy or $C_1$-$C_4$ alkylthio (e.g. methoxymethyl, 2-methoxyethoxymethyl, methylthiomethyl), tetrahydropyranyl, etc.

The term "halogen" in the halomethyl group includes chlorine, bromine and iodine. The lower alkoxycarbonyl group may have an alkyl moiety of not more than about 5 carbon atoms, and its specific examples are methoxycarbonyl, ethoxycarbonyl, n-propoxycarbonyl, isopropoxycarbonyl, n-butoxycarbonyl, t-butoxycarbonyl, etc. In the ar(lower)alkoxycarbonyl group wherein the aryl group is optionally substituted, the ar(lower)alkyl group may be, for instance, mono or diarylmethyl (e.g. benzyl, diphenylmethyl), and the substituent on the aryl group may be, for instance, $C_1$-$C_4$ alkoxy, $C_1$-$C_4$ alkyl, nitro, halogen or the like. Thus, specific examples of the ar(lower)alkoxycarbonyl group optionally substituted on the aryl group are benzyloxycarbonyl, p-nitrobenzyloxycarbonyl, o-nitrobenzyloxycarbonyl, p-methoxybenzyloxycarbonyl, diphenylmethyloxycarbonyl, etc. As the protecting group for the hydroxyl group in the protected hydroxymethyl group, there may be employed any conventional one used for protecting a hydroxyl group, and its specific examples are lower alkoxycarbonyl such as $C_1$-$C_5$ alkoxycarbonyl (e.g. t-butyloxycarbonyl), halo(lower)alkoxycarbonyl such as halo($C_1$-$C_5$)alkoxycarbonyl (e.g. 2-iodoethyloxycarbonyl, 2,2,2-trichloroethyloxycarbonyl), optionally substituted ar(lower)alkoxycarbonyl such as ar($C_1$-$C_5$-)alkoxycarbonyl optionally substituted with $C_1$-$C_4$ alkoxy, $C_1$-$C_4$ alkyl, nitro, halogen or the like (e.g. benzyloxycarbonyl, p-nitrobenzyloxycarbonyl, o-nitrobenzyloxycarbonyl, p-methoxybenzyloxycarbonyl, diphenylmethoxycarbonyl), tri(lower)alkylsilyl such as tri($C_1$-$C_4$)alkylsilyl (e.g. trimethylsilyl, t-butyldimethylsilyl), diaryl(lower)alkylsilyl such as diaryl($C_1$-$C_4$-)alkylsilyl (e.g. diphenylmethylsilyl), substituted methyl such as methyl substituted with $C_1$-$C_4$ alkoxy or $C_1$-$C_4$ alkylthio (e.g. methoxymethyl, 2-methoxyethoxymethyl, methylthiomethyl), tetrahydropyranyl, etc.

Among the beta-lactam compounds (I), those of the following formula are preferred:

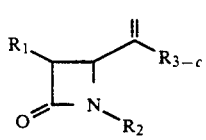
(I-a)

wherein $R_1$ and $R_2$ are each as defined above and $R_{3-c}$ is a methyl group, a hydroxymethyl group, a protected hydroxymethyl group, a lower alkoxycarbonyl group or an ar(lower)alkoxycarbonyl group wherein the aryl group is optionally substituted, or $R_2$ and $R_{3-c}$ are combined to form an oxaalkylene group and, when taken together with one nitrogen atom and two carbon atoms adjacent thereto, they represent a 6-membered cyclic aminoacetal group.

Most preferred are those of the following formula:

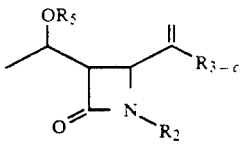

(I-b)

wherein $R_2$ and $R_{3-c}$ are each as defined above and $R_5$ is a hydrogen atom or a protective group for the hydroxyl group (i.e. a hydroxyl-protecting group).

The beta-lactam compounds (I) according to the invention are novel and characteristic in having a substituted ethenyl group at the 4-position of the beta-lactam skeleton.

Production of the beta-lactam compounds (I) are explained in detail below.

(1) A beta-lactam compound of the formula:

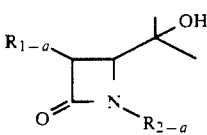

(II)

wherein $R_{1-a}$ is a hydrogen atom, a lower alkyl group or a 1-hydroxy(lower)alkyl group wherein the hydroxyl group is protected and $R_{2-a}$ is a hydrogen atom or a protective group for the nitrogen atom (i.e. a nitrogen-protecting group) is subjected to dehydration to give a beta-lactam compound of the formula:

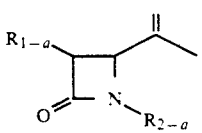

(I-1)

wherein $R_{1-a}$ and $R_{2-a}$ are each as defined above.

The dehydration may be accomplished by treatment of the compound (II) with a dehydrating agent in the presence or absence of a base, if necessary, in an inert solvent. As the dehydrating agent, there may be employed a halogenating agent (e.g. thionyl chloride, phosphorus oxychloride), a sulfonating agent (e.g. methanesulfonyl chloride, tosyl chloride), a water-eliminating agent (e.g. dicyclohexylcarbodiimide), etc. Examples of the base are triethylamine, pyridine, lutidine, N-dimethylaminopyridine, etc. As the inert solvent, there may be exemplified benzene, toluene, tetrahydrofuran, dioxane, diethyl ether, methylene chloride, chloroform, carbon tetrachloride, dimethylformamide, dimethylsulfoxide, hexamethylphosphorylamide, etc.

The dehydrating agent as well as the base may be used in sufficient amounts so as to proceed the reaction smoothly. No specific limitation is present on the reaction temperature, and cooling or heating may be adopted for suppressing or promoting the reaction. Usually, however, the dehydration may be carried out at a temperature of from about $-30°$ to $100°$ C.

(2) The beta-lactam compound (I-1) is subjected to halogenation to give a beta-lactam compound of the formula:

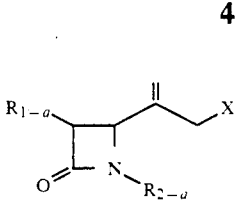

(I-2)

wherein $R_{1-a}$ and $R_{2-a}$ are each as defined above and X is a halogen atom.

The halogenation can be accomplished by treatment of the beta-lactam compound (I-1) with a halogenating agent in an inert solvent. The halogenating agent may be chosen from those as conventionally employed for halogenation at the allyl position. Preferred examples are molecular halogen (e.g. chlorine, bromine), hypohalogenous acid (e.g. hypochlorous acid, hypobromous acid), N-halosuccinimide (e.g. N-chlorosuccinimide, N-bromosuccinimide), chlorine monoxide, t-butyl hypochlorite, etc. Examples of the inert solvent are halogenated hydrocarbons (e.g. chloroform, methylene chloride, 1,2-dichloroethane, carbon tetrachloride), aromatic hydrocarbons (e.g. benzene, toluene), ethers (e.g. diethyl ether, tetrahydrofuran, dioxane), ethyl acetate, acetonitrile, dimethylformamide, etc. These may be used solely or in combination. In case of using chlorine or chlorine monoxide, which is gaseous at an ordinary temperature, as the halogenating gent, it may be introduced as such into the reaction system. However, it is favorably used in the form of a solution in a halogenated hydrocarbon.

The halogenating agent may be used in a sufficient amount to assure the smooth proceeding of the reaction and normally in an amount of 1 to 1.5 equivalents to 1 equivalent of the beta-lactam compound (I-1). Occasional cooling or heating of the reaction system is favored in order to control the reaction. In general, the reaction temperature may be from about $0°$ to $100°$ C.

Still, the halogen atom in the beta-lactam compound (I-2) may be substituted with any other halogen atom by treatment with an alkali metal salt of the other halogen atom (e.g. sodium iodide, potassium iodide, sodium bromide) in an inert solvent (e.g. acetone, acetonitrile, dimethylformamide).

(3) The beta-lactam compound (I-2) is subjected to hydrolysis to give a beta-lactam compound of the formula:

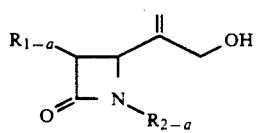

(I-3)

wherein $R_{1-a}$ and $R_{2-a}$ are each as defined above.

The hydrolysis may be effected by treatment of the compound (I-2) with water in the presence of a heavy metal ionic salt of low atomic valency in an inert solvent. The heavy metal ionic salt may be chosen from any one as conventionally employed for the conversion of allyl halide into allyl alcohol, and its examples are salts of $Cu^+$, $Ag^+$, $Hg^+$, $Tl^+$, $Cd^{++}$, etc. The anionic portion of such salt may be constituted with any one chosen from organic acids (e.g. trifluoroacetic acid, p-toluenesulfonic acid, methanesulfonic acid) and inorganic acids (e.g. sulfuric acid, pyrophosphoric acid). As the inert solvent, there may be exemplified dimethylformamide, dimethylsulfoxide, ethyl acetate, acetone, acetonitrile, methylene chloride, chloroform, tetrahydrofuran, dioxane, benzene, toluene, etc. Among them, dimethylsulfoxide, dimethylformamide and ethyl acetate are preferred.

The hydrolysis may be carried out under cooling or heating so as to control the reaction rate appropriately and is favorably effected at a temperature from room temperature to 100° C. The heavy metal, organic acid or inorganic acid may be used in a sufficient amount to assure the smooth proceeding of the reaction.

(4) The beta-lactam compound (I-3) is oxidized to give a beta-lactam compound of the formula:

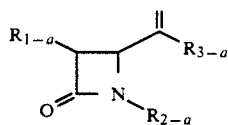
(I-4)

wherein $R_{1-a}$ and $R_{2-a}$ are each as defined above and $R_{3-a}$ is a formyl group or a carboxyl group.

The oxidation may be accomplished by a per se conventional oxidation procedure for conversion of a primary alcohol into the corresponding aldehyde or carboxylic acid. For instance, it may be carried out by treatment with an oxidizing agent chosen from chromic oxidizing agents (e.g. chromium (VI) oxide-sulfuric acid, chromium (VI) oxideacetic acid, chromium (VI) oxide-pyridine complex, pyridinium chromochromate, pyridinium dichromate), dimethylsulfoxide with oxalyl chloride, sulfur trioxide, acetic anhydride or the like, hypochlorite or the like, permanganates, manganese dioxide, silver compounds (e.g. silver oxide), etc. in an inert solvent (e.g. chloroform, methylene chloride, 1,2-dichloroethane, carbon tetrachloride, acetone, acetonitrile, acetic acid, isopropanol, t-butanol, water, benzene, toluene, diethyl ether, tetrahydrofuran).

Still, the oxidation of the compound (I-3) into the carboxylic acid may be accomplished by the use of a single oxidizing agent or stepwise through the aldehyde by the use of different kinds of oxidizing agents.

The oxidizing agent is favorably used in such an amount that can assure the smooth proceeding of the reaction. Further, occasional cooling or heating of the reaction system is favored in order to control the reaction appropriately. Usually, the temperature in the oxidation may be from about −78° to 60° C.

(5) The beta-lactam compound of the formula:

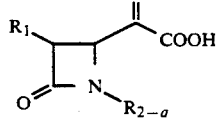
(I-4')

wherein $R_1$ and $R_{2-a}$ are each as defined above is subjected to esterification to give a beta-lactam compound of the formula:

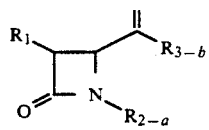
(I-5)

wherein $R_1$ and $R_{2-a}$ are each as defined above and $R_{3-b}$ is a lower alkoxycarbonyl group or an ar(lower)alkoxycarbonyl group.

The esterification of the beta-lactam compound (I-4') may be accomplished by a per se conventional procedure for conversion of a carboxylic acid into the corresponding ester such as treatment with a lower alkanol or an ar(lower)alkanol in the presence of an acid such as a mineral acid (e.g. sulfuric acid, hydrochloric acid), a sulfonic acid (e.g. methanesulfonic acid, p-toluenesulfonic acid) or a Lewis acid (e.g. boron trifluoride etherate), treatment with a lower alkyl halide or ah ar(lower)alkyl halide in the presence of a base such as an inorganic base (e.g. potassium carbonate, potassium hydroxide, sodium hydroxide) or an organic base (e.g. triethylamine, diisopropylethylamine, pyridine, 2,6-lutidine, 1,8-diazabicyclo[5.4.0]-7-undecene (DBU)), treatment with a lower alkanol or an ar(lower)alkanol in the presence of a dehydrating agent (e.g. dicyclohexylcarbodiimide) or treatment with a diazo(lower) alkane. These treatments are usually effected in an inert solvent, which may be chosen from chloroform, methylene chloride, 1,2-dichloroethane, carbon tetrachloride, dimethylformamide, tetrahydrofuran, dioxane, diethyl ether, acetonitrile, benzene, toluene, etc.

The reagents such as the acid, the base and the dehydrating agent are favorably used in such amounts that can assure the smooth proceeding of the reaction. Further, occasional cooling or heating of the reaction system is favored in order to control the reaction. Normally, the reaction temperature resides between about 0° to 150° C.

(6) A beta-lactam compound of the formula:

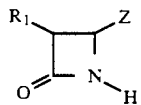
(III)

wherein $R_1$ is as defined above and Z is a leaving group is reacted with the silylketeneacetal derivative of the compound of the formula:

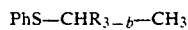
PhS—CHR$_{3-b}$—CH$_3$  (IV)

wherein $R_{3-b}$ is as defined above and Ph is a phenyl group, followed by oxidation of the thiophenyl group and then heating to give a beta-lactam of the formula;

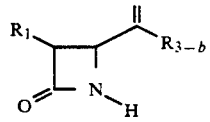
(I-5')

wherein $R_1$ and $R_{3-b}$ are each as defined above.

The leaving group in the compound (III) may be, for instance, halogen (e.g. chlorine, bromine, iodine), acetoxy, mesyloxy, p-tolyloxy or the like.

The initial reaction may be carried out in the presence of an acid, usually in an inert solvent. As the acid, there may be used a Lewis acid, of which preferred examples are boron trifluoride etherate, silver borofluoride, zinc iodide, etc. Trimethylsilyl trifluorate is also usable as the acid. Examples of the inert solvent are halogenated hydrocarbons (e.g. chloroform, methylene chloride, 1,2-dichloroethane, carbon tetrachloride), ethers (e.g.

diethyl ether, tetrahydrofuran, dioxane,), aromatic hydrocarbons (e.g. benzene, toluene), etc.

The acid and the silylketene acetal derivative of the compound (IV) are used in such amounts that can assure the smooth proceeding of the reaction. Preferably, they are respectively used in 1 to 4 equivalents to 1 equivalent of the compound (III). Further, occasional cooling or heating of the reaction system is favored in order to control the reaction. In general, the reaction temperature may be within a range of about 0° to 50° C.

(7) The beta-lactam compound of the formula:

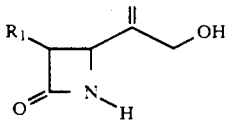
(I-3')

wherein $R_1$ is as defined above is subjected to dehydration in the presence of a carbonyl compound of the formula:

(V)

wherein $R_1^0$ and $R_2^0$ are each a lower alkyl group, or they may be combined together to form an alkylene chain and, when taken together with the carbonyl carbon atom, they represent a 5 to 7-membered cyclic group or to amino-acetalation in the presence of the dialkylacetal derivative of the carbonyl compound (V) to give a beta-lactam compound of the formula:

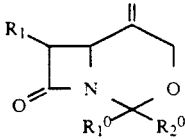
(I-7)

wherein $R_1$, $R_1^0$ and $R_2^0$ are each as defined above,

Said dehydration or aminoacetalation may be accomplished by any conventional procedure for conversion of an aminoalcohol into the corresponding aminoacetal, for instance, treatment of the beta-lactam compound (I-3') with the carbonyl compound (V) or its dialkylacetal derivative in the presence of an acid, if necessary, in an inert solvent. As the acid, there may be used a sulfonic acid (e.g. methanesulfonic acid, p-toluenesulfonic acid), a mineral acid (e.g. sulfuric acid, hydrochloric acid), a Lewis acid (e.g. zinc chloride, boron trifluoride etherate), boron tribromide) or the like. Examples of the inert solvent are benzene, toluene, tetrahydrofuran, dioxane, diethyl ether, methylene chloride, chloroform, 1,2-dichloroethane, dimethylformamide, dimethylsulfoxide, etc.

The carbonyl compound (V) or its dialkylacetal derivative and the acid are desired to be used in such amounts that can assure the smooth proceeding of the reaction. Further, occasional cooling or heating of the reaction system is favored in order to control the reaction appropriately. Usually, the reaction temperature may be from about 0° to 100° C.

(8) The beta-lactam compound (I-3) is subjected to protection for the hydroxyl group, whereby a beta-lactam compound of the formula:

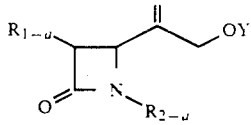
(I-6)

wherein $R_{1-a}$ and $R_{2-a}$ are each as defined above and Y is a protective group for the hydroxyl group is obtained.

The protection may be accomplished, for instance, by treating the beta-lactam compound (I-3) with a halide in the presence of a base or with an unsaturated cyclic ether (e.g. dihydropyran) in the presence of an acid, if necessary, in an inert solvent. As the halide, there may be used the one chonsen from lower alkoxycarbonyl halides (e.g. ethyl chloroformate, isopropyl chloroformate, sec-butyl chloroformate), halo(lower)alkoxycarbonyl halides (e.g. 2,2,2-trichloroethyl chloroformate, 2-iodoethyl chloroformate), ar(lower)alkyloxycarbonyl halides (e.g. benzyl chloroformate, p-nitrobenzyl chloroformate), lower alkanoyl halides (e.g. acetyl chloride, propionyl chloride), arylcarbonyl halides (e.g. benzoyl chloride), tri(lower)alkylsilyl halides (e.g. trimethyl chlorosilane, t-butyldimethyl chlorosilane), substituted methyl halides (e.g. chloromethyl methyl ether, chloromethyl methyl thioether), etc.

The starting compound (II) is obtainable by various procedures, of which a typical example is representable by the following reaction scheme:

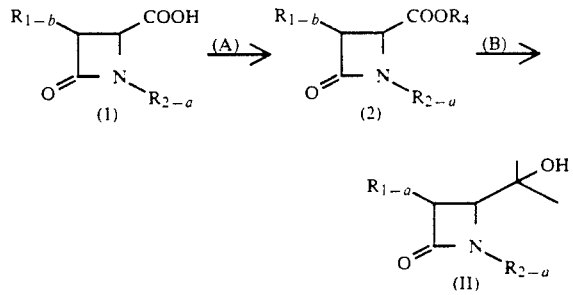

wherein $R_{1-a}$ and $R_{2-a}$ are each as defined above, $R_{1-b}$ is a hydrogen atom, a lower alkyl group or a 1-hydroxy(lower)alkyl group and $R_4$ is a lower alkyl group.

In the above reaction scheme, the step (A) comprises conversion of the carboxylic acid (1), obtainable by a conventional procedure (e.g. EP 0070204), into the corresponding ester (2) by a per se conventional procedure such as esterification of the former with an alkyl halide in the presence of a base or dehydration of the former with a lower alkanol in the presence of a dehydrating agent. The step (B) comprises reduction of the ester (2) to the beta-lactam compound (II) by a per se conventional procedure such as treatment of the former with an organic metal compound (e.g. methylmagnesium halide, methyl lithium), if necessary, in an inert solvent and, in case of $R_{1-b}$ being a 1-hydroxy(lower)alkyl group, subjecting the resultant product to protection for the hydroxyl group.

The starting compound (III) can be produced by various procedures including those as disclosed, for instance, in EP 00702024 or Chem. Pharm. Bull., 29, 2899-2909 (1981).

The beta-lactam compound (I) as produced above can be converted stereospecifically into a carbapenem compound of the formula:

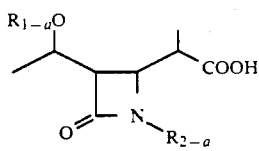

wherein $R_{1-a}$ and $R_{2-a}$ are each as defined above, which is described in EP-0071908A and useful as an intermediate for the synthesis of 1-methylcarbapenem derivatives having an excellent antimicrobial activity, by various procedures, of which some typical examples are illustratively shown below.

Procedure (1):

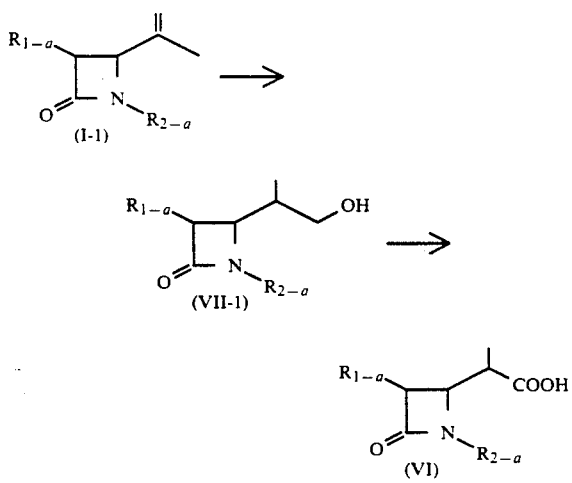

wherein $R_{1-a}$ and $R_{2-a}$ are each as defined above.

The beta-lactam compound (-1) is subjected to hydroboration, followed by oxidation to give predominantly the alcohol (VII-1) wherein the carbon atom at the 5-position has an S-configuration, which is then subjected to oxidation, optionally followed by removal of the protective group for the amino group to give the carboxylic acid (VI) wherein the carbon atom at the 5-position has an S-configuration.

The above conversions may be accomplished by a per se conventional procedure for conversion of an olefin into the corresponding alcohol. For instance, the beta-lactam compound (I-1) is treated with a hydroborating agent (e.g. 9-borobiscyclo[3.3.1]nonane (9-BBN), hexylborane, dicyclohexylborane) in an inert solvent such as an ether (e.g. diethyl ether, tetrahydrofuran) preferably at a temperature of 0° to 50° C., followed by treatment with hydrogen peroxide in the presence of a base (e.g. sodium hydroxide) preferably at a temperature of room temperature to 100° C.

The amounts of the hydroborating agent and hydrogen peroxide are desired to be used in such amounts that can assure the smooth proceeding of the reaction. Further, occasional cooling or heating of the reaction system is favored in order to control the reaction rate appropriately.

Procedure (2):

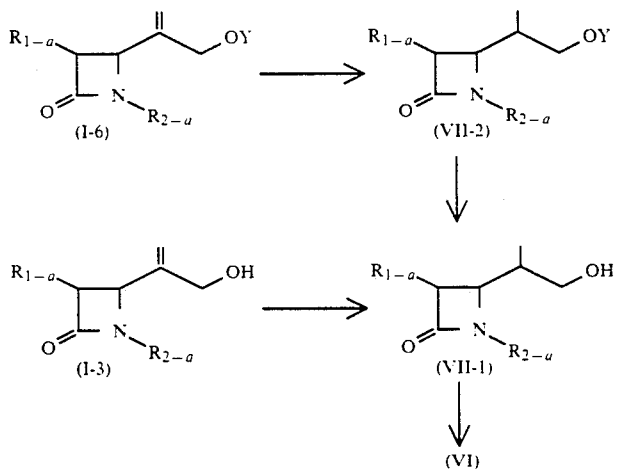

wherein $R_{1-a}$ and $R_{2-a}$ and Y are each as defined above.

The beta-lactam compound (I-3) or (I-6) is subjected to hydrogenation to give the compound (VII-1) or (VII-2). The compound (VII-1) thus obtained or produced from the compound (VII-2) by removal of the hydroxyl-protecting group Y is then oxidized to the compound (VI) optionally with previous removal of the nitrogen-protecting group $R_{2-a}$.

For the hydrogenation, there may be adopted a conventional reduction method for addition of hydrogen atoms to a double bond, preferably catalytic hydrogenation under a hydrogen atmosphere. As the catalyst, the use of a transition metal catalyst (e.g. platinum oxide, platinum-activated carbon, palladium-activated carbon, rhodium-activated carbon) is favorable from the viewpoint of stereo-specificity. The hydrogenation is usually effected in an inert solvent, of which examples are methanol, ethanol, ethyl acetate, tetrahydrofuran, dioxane, acetonitrile, cyclohexane, dimethylformamide, etc. A mixture of any of these organic solvents with water or phosphate buffer is also usable as the inert solvent. Even when the hydroxyl-protecting group and/or the nitrogen-protecting group can be eliminated by catalytic hydrogenation, the hydrogenation is applicable by the use of an appropriate catalyst such as platinum oxide or platinum-activated carbon in an inert solvent such as acetonitrile, dimethylformamide, ethyl acetate or a mixture of any of these organic solvents and water. In order to enhance the selectivity, the introduction of an amine into the reaction system is preferred. Examples of the amine are pyridine and tertiary amines (e.g. triethylamine, tripropylamine, diisopropylethylamine, N,N-dimethylaniline), among which pyridine, triethylamine, diisopropylethylamine, etc. are particularly favored. Usually, the amounts of the catalyst and the amine may be from about 0.2 to 0.5 part by weight to one part by weight of the starting compound (I) and from about 1.1 to 10 equivalents to one equivalent of the metal in the catalyst. The double bond is effected by reduction as employed conventionally and, a catalytic reduction under hydrogen atmosphere is most preferably employed. The reaction temperature may be normally from about 0° to 50° C. under a pressure of atmospheric pressure to 5 kg/cm².

When $R_{2-a}$ in the compound (I-3) or (I-6) is a nitrogen-protecting group, the hydrogenation gives predominantly the compound (VII-1) or (VII-2) wherein the carbon atom at the 5-position has an R-configuration. When $R_{2-a}$ is a hydrogen atom, there is predominantly obtainable a compound (VII-1) or (VII-2) wherein the carbon atom at the 5-position has an S-configuration.

Procedure (3):

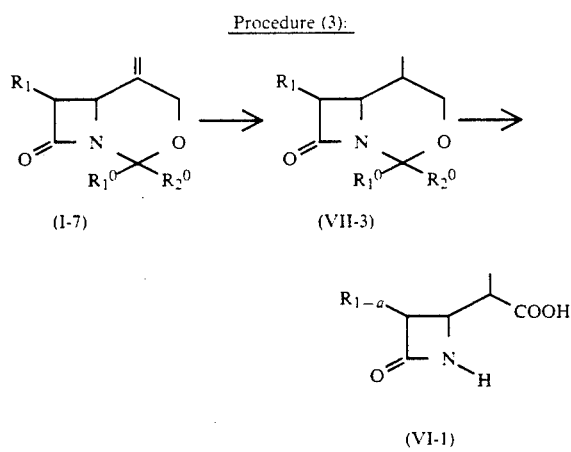

wherein $R_1$, $R_{1-a}$, $R_1^0$ and $R_2^0$ are each as defined above.

The beta-lactam compound (I-7) is subjected to hydrogenation to give the compound (VII-3). When $R_1$ represents a 1-hydroxy(lower)alkyl group, the resulting product is subjected to protection of the hydroxyl group, followed by oxidation such as described in EP 0071908 to give the compound (VI-1).

The hydrogenation may be accomplished by a per se conventional procedure as adopted for addition of hydrogen atoms to a double bond and, for instance, in the same manner as described in connection with Procedure (2), particularly by catalytic hydrogenation using hydrogen in the presence of a catalyst. Catalysts and inert solvents preferred from the viewpoint of stereospecificity are those as mentioned in Procedure (2). Catalytic hydrogenation of the compound (I-7) affords predominantly the compound (VII-3) wherein the carbon atom at the 5-position has an R-configuration.

Procedure (4):

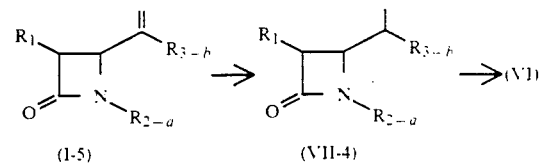

wherein $R_1$, $R_{2-a}$ and $R_{3-b}$ are each as defined above.

The beta-lactam compound (I-5) is subjected to hydrogenation to give the compound (VII-4). When $R_1$ is a 1-hydroxy(lower)alkyl group, the resulting product is subjected to protection for the hydroxyl group, followed by conversion of the ester group into a carboxyl group to give the compound (VI).

The hydrogenation may be carried out by a per se conventional procedure for addition of hydrogen atoms to a double bond and, for instance, in the same manner as described in connection with Procedure (2), particularly by catalytic reduction using hydrogen in the presence of a catalyst or by reduction with a hydrogenating agent such as a metal hydride complex in the presence of a transition metal salt.

Catalysts and inert solvents preferably usable in the catalytic reduction are those as mentioned in, Procedure (2).

Reduction with a hydrogenating agent may be carried out by treatment with a metal hydride complex (e.g. sodium borohydride) in the presence of a transition metal salt (e.g. salts of nickel, copper, cobalt, palladium), usually in an inert solvent such as alcohols (e.g. methanol, ethanol, isopropanol), tetrahydrofuran or water. The amounts of the transition metal salt and of the metal hydride complex are respectively from about 0.05 to 0.5 equivalent and from about 5 to 15 equivalents to one equivalent of the starting compound (I). Further, occasional cooling or heating of the reaction system is favored in order to control the reaction. In general, the reaction temperature may be within a range of about 0° to 50° C.

When $R_{2-a}$ in the compound (I-5) is a nitrogen-protecting group, the hydrogenation affords predominantly the compound (VII-4) wherein the carbon atom at the 5-position takes an R-configuration irrespective of being carried out by catalytic hydrogenation or reduction with a hydrogenating agent. When $R_{2-a}$ is a hydrogen atom, the compound (VII-4) having an S-configuration at the 5-position is predominantly produced.

As stated above, the beta-lactam compound of the invention can afford selectively the compound (VI) having either a 5S-configuration or a 5R-configuration useful as an intermediate in the synthesis of the 1-methylcarbapenem compound by stereospecific reduction or hydroborationoxidation.

Practical and presently preferred embodiments of the invention for production of the beta-lactam compound (I) are illustratively shown in the following Examples and Reference Examples, wherein the abbreviations used therein have the following meanings:

Z: benzyloxycarbonyl
DAM: di(p-anisyl)methyl
Me: methyl
Et: ethyl
Ph: phenyl
THP: tetrahydropyranyl MOM: methoxymethyl
t-Bu: t-butyl
TCC: 2,2,2-trichloroethyloxycarbonyl
PNZ: p-nitrobenzyloxycarbonyl.

EXAMPLE 1-(1)

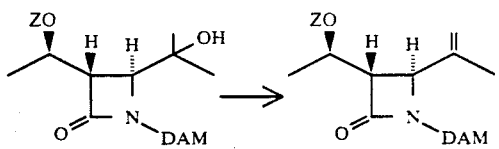

A solution of (3S,4S)-4-(1-hydroxy-1-methylethyl)-3-(1-(R)-benzyloxycarbonyloxyethyl)-1-di(p-anisyl)methyl-2azetidinone (30 g) in dry toluene (350 ml) was treated with thionyl chloride (9.0 g) at 20°–30° C. for 5 hours in the presence of pyridine (10 ml). Water (100 ml) was added to quench the reaction at 10°–25° C. The organic layer was separated, washed with water and dried over anhydrous sodium sulfate. Filtration and concentration of the filtrate in vacuo gave an oily residue, which was crystallized from a mixture of cyclohexane and ethyl acetate to yield (3S,4S)-4-(1-methylethenyl)-3-(1-(R)-benzyloxycarbonyloxyethyl)-1-di(p-anisyl)methyl-2-azetidinone. m.p., 117°–118° C.

EXAMPLE 1-(2)

The following compounds were obtained by the similar procedure to that described in Example 1-(1).

| No. | R₄ | Spectra data | |
|---|---|---|---|
| 1 | TCC | IR $\nu_{max}^{neat}$ (cm$^{-1}$): | 1760, 1610, 1515, 1375, 1250, 1175, 1122, 1030, 820. |
| | | NMR δ (CDCl₃): | 1.42(3H, d, J=6.5Hz), 1.53(3H, bs), 3.10(1H, dd, J=2 and 6Hz), 3.78(6H, s), 4.12(1H, d, J=2Hz), 4.79 (2H, s), 5.51(1H, bs). |
| 2 | PNZ | IR $\nu_{max}^{neat}$ (cm$^{-1}$): | 1750, 1610, 1510, 1378, 1345, 1300, 1250, 1175, 1028, 845, 750. |
| | | NMR δ (CDCl₃): | 1.40(3H, d, J=6.5Hz), 1.52(3H, bs), 3.08(1H, dd, J=2 and 6Hz), 3.74(6H, s), 4.09(1H, d, J=2Hz), 5.20 (2H, s), 5.49(1H, s). |

EXAMPLE 2

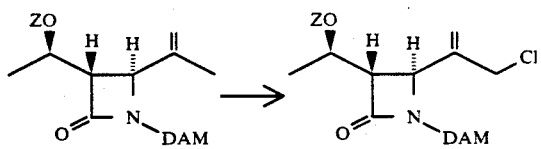

(3S,4S)-4-(1-Methylethenyl)-3-(1-(R)-benzyloxycarbonyloxyethyl)-1-di(p-anisyl)methyl-2-azetidinone (200 g) was dissolved in ethyl acetate (3 liters), and a solution of chlorine in carbon tetrachloride (3.85%, 870 g) was added dropwise thereto at room temperature over a period of 15 minutes, followed by stirring for 1 hour. Water (1 liter) and then 10% aqueous sodium thiosulfate (50 ml) were poured into the reaction mixture, which was stirred for 0.5 hour and allowed to stand. The organic layer was washed successively with saturated sodium bicarbonate and brine and dried over anhydrous sodium sulfate. Filtration and concentration of the filtrate in vacuo gave (3S,4S)-4-(1-chloromethylethenyl)-3-(1-(R)-benzyloxycarbonyloxyethyl)-1-di(p-anisyl)methyl-2-azetidinone. m.p., 84°–85° C.

EXAMPLE 3-(1)

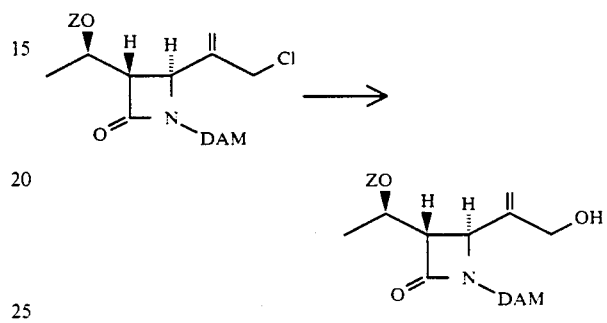

To a solution of (3S,4S)-4-(1-chloromethylethenyl)-3-(1-(R)-benzyloxycarbonyloxyethyl)-1-di(p-anisyl)methyl-2-azetidinone (20 g) in dimethylsulfoxide (160 ml) were successively added water (40 ml), cuprous oxide (6.76 g) and p-toluenesulfonic acid (7.6 g), and the resultant mixture was warmed to 50° to 55° C. and stirred for 2 hours at the same temperature. After cooling down to room temperature, 1% aqueous phosphoric acid (90 ml) and ethyl acetate (200 ml) were poured into the reaction mixture, followed by stirring for 0.5 hour. An insoluble material was removed by filtration over celite and washed 3 times with ethyl acetate (20 ml). The filtrate and the washings were combined together, and the aqueous layer was separated from the organic layer and extracted with ethyl acetate (200 ml). The organic layer and the extract were combined together, washed with brine and dried over anhydrous sodium sulfate. After filtration and concentration of the filtrate in vacuo, the concentrate was crystallized from a mixture of toluene and n-hexane (1:1) to give crystals of (3S,4S)-4-(1-hydroxymethylethenyl)-3-(1-(R)-benzyloxycarbonyloxyethyl)- 1-di(p-anisyl)methyl-2-azetidinone. m.p., 118°–120° C.

EXAMPLE 3-(2)

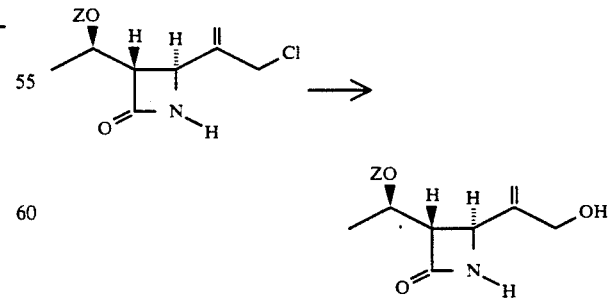

To a solution of (3S,4S)-4-(1-chloromethylethenyl)-3-(1-(R)-benzyloxycarbonyloxyethyl)-2-azetidinone (100 g) in dimethylsulfoxide (800 ml) and water (200 ml) were added cuprous oxide (57.6 g) and p-toluenesulfonic acid (107 g), and the resultant mixture was stirred at 50° C. for 1.5 hours and then cooled down with ice-cooling. Brine (3 liters), 2N hydrochloric acid (1 liter), ethyl acetate (2 liters) and diethyl ether (2 liters) were poured into the reaction mixture, followed by stirring for 0.5 hour. The aqueous layer was extracted with a mixture of ethyl acetate (1 liter) and diethyl ether (1 liter). The combined extracts were washed successively with brine (2 liters), 5% sodium bicarbonate (2 liters) and brine (2 liters) and dried over anhydrous sodium sulfate. Filtration and concentration of the filtrate in vacuo gave (3S,4S)-4-(1-hydroxymethylethenyl)-3-(1-(R)-benzyloxycarbonyloxyethyl)-2-azetidinone.

IR $v_{max}^{neat}$(cm$^{-1}$) 3300, 1745, 1450, 1378, 1258, 1135, 905.

NMR δ (CDCl$_3$) 1.43 (3H, d, J=6.5 Hz), 3.14 (1H, dd, J=2 and 8 Hz), 4.09 (2H, bs), 4.18 (1H, bd, J=2 Hz), 5.12 (1H, m), 5.15 (2H, s), 6.57 (1H, bs), 7.36 (5H, s).

EXAMPLE 4-(1)

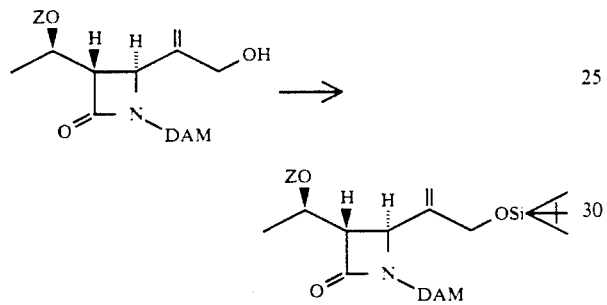

A solution of (3S,4S)-4-(1-hydroxymethylethenyl)-3-(1-(R)-benzyloxycarbonyloxyethyl)-1-di(p-anisyl)methyl-2-azetidinone (20 g) and imidazole (5.6 g) in dry dimethylformamide (45 ml) was treated with t-butyl dimethyl chlorosilane (6.77 g) at room temperature for 2 hours. The reaction mixture was diluted with cold water (200 ml) and ethyl acetate (150 ml). The aqueous layer was extracted with ethyl acetate (150 ml). The combined extracts were washed successively with 5% hydrochloric acid solution (80 ml×2) and brine (80 ml), and dried over anhydrous sodium sulfate. After filtration and concentration of the filtrate in vacuo, the concentrate was crystallized from isopropanol to give crystals of (3S,4S)-4-(1-t-butyldimethylsilyloxymethylethenyl)-3-(1-(R)-benzyloxycarbonyloxyethyl)-1-di(p-anisyl)methyl-2-azetidinone. m.p., 90°-92° C.

EXAMPLE 4-(2)

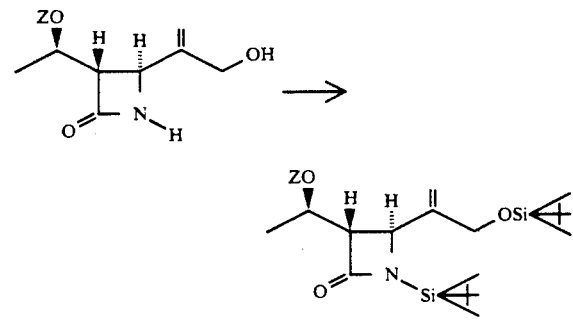

t-Butyldimethylchlorosilane (18.1 g) was added to an ice-cold stirred solution of (3S,4S)-4-(1-hydroxymethylethenyl)-3-(1-(R)-benzyloxycarbonyloxyethyl)-2-azetidinone (12.12 g) and triethylamine (22.26 ml) in dry dimethylformamide (120 ml). After stirring for 3 hours at room temperature, the reaction mixture was diluted with ethyl acetate (360 ml), washed with brine and dried over anhydrous sodium sulfate. Filtration and concentration of the filtrate in vacuo gave an oily residue, which was purified by silica gel chromatography to yield (3S,4S)-4-(1-t-butyldimethylsilyloxyethenyl)-3-(1-(R)-benzyloxycarbonyloxyethyl)-1-t-butyldimethylsilyl-2-azetidinone.

IR $v_{max}^{neat}$ (cm$^1$) 1750, 1462, 1380, 1260, 1135, 835.

NMR δ (CDCl$_3$) 0.05 (6H, s), 0.07 (3H, s), 0.28 (3H, s), 0.90 (9H, s), 0.95 (9H, s), 1.39 (3H, d, J=6.4 Hz), 3.19 (1H, dd, J=2.6 and 6.6 Hz), 4.08 (1H, d, J=2.6 Hz), 4.14 (2H, s), 5.14 (2H, s), 7.35 (5H, s).

EXAMPLE 4-(3)

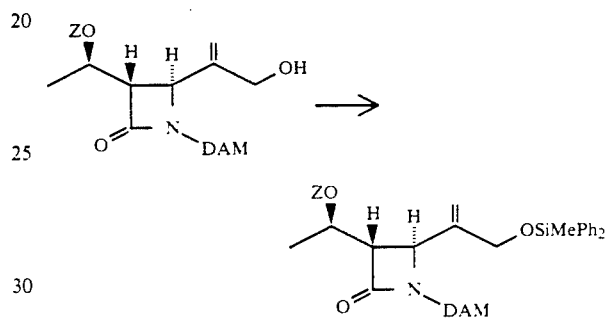

Following the procedure as described in Example 4-(1) but replacing t-butyl dimethylchlorosilane by diphenyl methylchlorosilane, (3S,4S)-4-(1-diphenylmethylsilyloxymethylethenyl)-3-(1-(R)-benzyloxycarbonyloxyethyl)-1-di(p-anisyl)methyl-2-azetidinone was obtained.

NMR δ (CDCl$_3$): 1.29 (3H, d, J=6.4 Hz), 3.16 (1H, dd, J=2.4 and 5.5 Hz), 3.67 (3H, s), 3.70 (3H, s), 4.00 (2H, br, s), 4.15 (1H, d, J=2.2 Hz), 5.08 (1H, s), 5.10 (1H, m), 5.12 (2H, d, J=1.1 Hz), 5.24 (1H, s), 5.39 (1H, s), 7.35 (5H, s), 7.30-7.59 (10H).

EXAMPLE 5-(1)

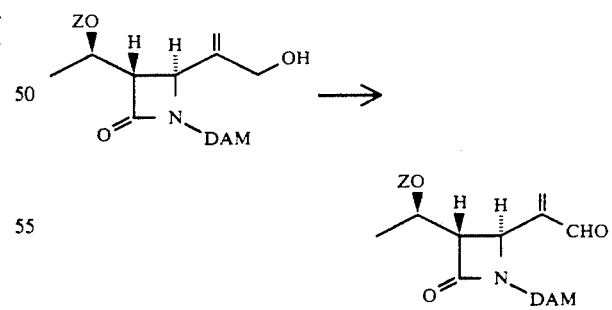

To a solution of oxalyl chloride (8.5 ml) in dry dichloromethane (212 ml) was added dropwise a mixture of dimethylsulfoxide (14.5 ml) and dichloromethane (42.5 ml) at −50° C., and the resultant mixture was stirred for 10 minutes at the same temperature as above. A solution of (3S,4S)-4-(1-hydroxymethylethenyl)-3-(1-(R)-benzyloxycarbonyloxyethyl)-1-di(p-anisyl)methyl-2-azetidinone (45 g) in dry dichloromethane (400 ml) was added dropwise thereto at −50° C. or less over a period of 15 minutes, followed by stirring for 15 minutes. Triethylamine (64 ml) was then dropwise added thereto, and the reaction mixture was warmed to room temperature, diluted with cold water (480 ml) and acidified with 6N hydrochloric acid (65 ml). The organic layer was washed successively with brine (200 ml×3), 2% sodium bicarbonate (200 ml) and then brine (200 ml) and dried over anhydrous sodium sulfate. Filtration and concentration of the filtrate in vacuo gave (3S,4S)-4-(1-formylethenyl)-3-(1-(R)-benzyloxycarbonyloxyethyl)-1-di(p-anisyl)methyl-2-azetidinone.

IR $\nu_{max}^{neat}$ (cm$^1$): 1760, 1695, 1620, 1520, 1255, 1185, 1030.

NMR δ (CDCl$_3$): 1.29 (3H, d, J=6.5 Hz), 3.09 (1H, dd, J=2.4 and 5.5 Hz), 3.61 (6H, s), 4.55 (1H, bs), 5.11 (2H, s), 5.57 (1H, s), 5.76 (1H, s), 6.03 (1H, s), 7.29 (5H, s), 9.22 (1H, s).

EXAMPLE 5-(2)

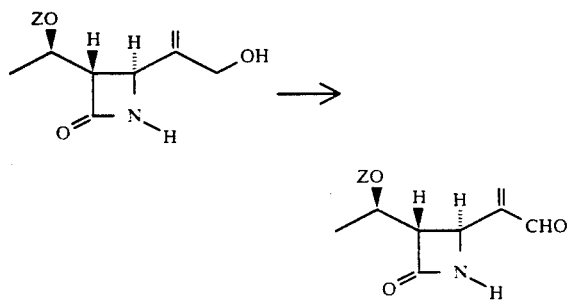

Following the procedure as described in Example 5-(1) but replacing the starting material by (3S,4S)-4-(1-hydroxymethylethenyl)-3-(1-(R)-benzyloxycarbonyloxyethyl)-2-azetidinone, there was obtained (3S,4S)-4-(1-hydroxyformylethenyl)-3-(1-(R)-benzyloxycarbonyloxyethyl)-2-azetidinone.

IR $\nu_{max}^{neat}$ (cm$^1$): 3300, 1745, 1690, 1450, 1380, 1255, 1140, 745, 692.

NMR δ (CDCl$_3$): 1.46 (3H, d, J=6.5 Hz), 3.10 (1H, dd, J=2 and 7 Hz), 4.57 (1H, d, J=2 Hz), 5.17 (2H, AB$_q$, J=9 Hz), 6.17 (1H, s), 6.48 (1H, s), 7.36 (5H, s), 9.60 (1H, s).

EXAMPLE 6

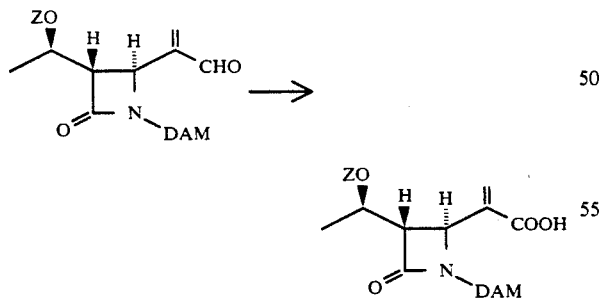

(3S,4S)-4-(1-Formylethenyl)-3-(1-(R)-benzyloxycarbonyloxyethyl)-1-di(p-anisyl)methyl-2-azetidinone (4.5 g) was dissolved in t-butanol (380 ml). After addition of 2-methyl-2-butene (42.5 ml) thereto, there was dropwise added an aqueous solution (72.3 ml) of sodium chlorite (7.15 g) and disodium hydrogenphosphate (7.15 g). The resulting mixture was stirred at room temperature for 1 hour and concentrated in vacuo at 40° C. or lower. The concentrate was diluted with ethyl acetate (150 ml) and water (75 ml), and the organic layer was separated. The aqueous layer was extracted with ethyl acetate (80 ml), and the combined ethyl acetate layer was washed with brine (150 ml) and extracted with a saturated sodium bicarbonate solution (150 ml). The alkaline layer was acidified with conc. hydrochloric acid under ice-cooling and extracted with ethyl acetate. The extracts were washed with brine and dried over anhydrous sodium sulfate. Filtration and concentration of the filtrate in vacuo gave (3S,4S)-4-(1-carboxyethenyl)-3-(1-(R)-benzyloxycarbonyloxyethyl)-1-di(p-anisyl)methyl-2-azetidinone.

IR $\nu_{max}^{neat}$ (cm$^1$): 1755, 1620, 1520, 1255, 1185, 1035.

NMR δ (CDCl$_3$): 1.39 (3H, d, J=6.5 Hz), 3.29 (1H, dd, J=2 and 5.5. Hz), 3.70 (6H, s), 4.56 (1H, d, J=2 Hz), 5.18 (2H, s), 5.61 (1H, s), 5.68 (1H, s), 6.22 (1H, s), 7.38 (5H, s).

EXAMPLE 7

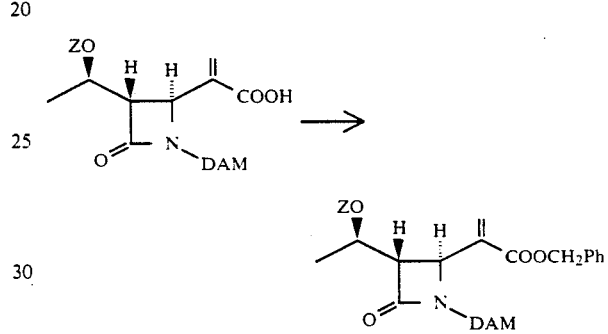

A solution of (3S,4S)-4-(1-carboxyethenyl)-3-(1-(R)-benzyloxycarbonyloxyethyl)-1-di(p-anisyl)methyl-2-azetidinone (3.7 g) in acetone (60 ml) was treated with benzyl bromide (1.4 g) in the presence of anhydrous potassium carbonate (1.88 g) under reflux for 2 hours. The reaction mixture was cooled down to room temperature, filtered to remove insoluble materials and concentrated in vacuo. The concentrate was diluted with ethyl acetate, washed with water and dried over anhydrous sodium sulfate. Filtration and concentration of the filtrate in vacuo gave (3S,4S)-4-(1-benzyloxycarbonylethenyl)-3-(1-(R)-benzyloxycarbonyloxyethyl)-1-di(p-anisyl)methyl-2-azetidinone.

IR $\nu_{max}^{neat}$ (cm$^1$): 1755, 1720, 1610, 1510, 1380, 1250, 1175, 1150, 1030.

NMR δ (CDCl$_3$): 1.37 (3H, d, J=6.5 Hz), 3.31 (1H, dd, J=2 and 5.5 Hz), 3.67 (3H, s), 3.70 (3H, s), 4.56 (1H, d, J=2 Hz), 5.08 (2H, s), 5.17 (2H, s), 5.58 (2H, s), 6.11 (1H, s), 7.33 (5H, s), 7.37 (5H, s).

EXAMPLE 8

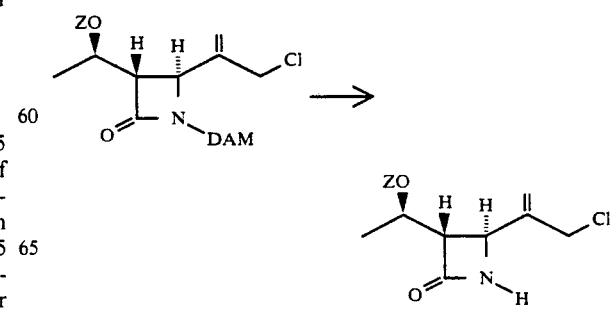

To a solution of (3S,4S)-4-(1-chloromethylethenyl)-3-(1-(R)-benzyloxycarbonyloxyethyl)-1-di(p-anisyl)methyl-2-azetidinone (320 g) in a mixture of acetonitrile and water (9 : 1) (3.8 liters) was added a solution of ceric ammonium nitrate (702 g) in a mixture of acetonitrile and water (9 : 1) (2 liters) at 5° C. or lower, followed by stirring for 30 minutes. The reaction mixture was diluted with water (5.2 liters) and extracted with ethyl acetate (3.4 liters). The aqueous layer was extracted with a mixture of ethyl acetate (1.7 liters), diethyl ether (1.7 liters) and benzene (1.7 liters). The combined extracts were washed successively with brine, 51% sodium bicarbonate and brine, and dried over anhydrous sodium sulfate. Filtration and concentration of the filtrate in vacuo gave an oily residue, which was dissolved in methanol (1.5 liters) with warming and allowed to cool gradually. After filtration to remove crystals, the filtrate was concentrated in vacuo to give an oily residue, which was purified by silica gel chromatography to yield (3S,4S)-4-(1-chloromethylethenyl)-3-(1-(R)-benzyloxycarbonyloxyethyl)-2-azetidinone.

IR $\nu_{max}^{neat}$ (cm$^{-1}$): 1750, 1450, 1380, 1260, 1135.

NMR δ (CDCl$_3$).: 1.46 (3H, d, J=6.0 Hz), 3.12 (1H, dd, J=2.5 and 8.5 Hz), 4.06 (2H, s), 4.31 (1H, d, J=2.5 Hz), 5.16 (2H, s), 5.30 (2H, bs), 6.37 (1H, bs), 7.36 (5H, s).

EXAMPLE 9-(1)

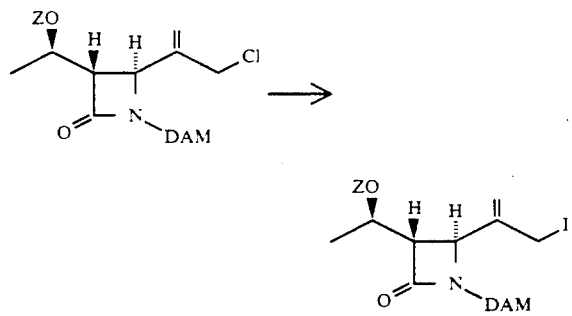

To a solution of (3S,4S)-4-(1-chloromethylethenyl)-3-(1-(R)-benzyloxycarbonyloxyethyl)-1-di(p-anisyl)methyl-2-azetidinone (2.24 g) in acetone (25 ml) was added sodium iodide (1.2 g), and the resultant mixture was stirred at room temperature for 5 hours and concentrated in vacuo to make a volume of about 10 ml. The concentrated solution was diluted with benzene (50 ml) and diethyl ether (50 ml), washed successively with 5% sodium bicarbonate and water and dried over anhydrous sodium sulfate. Filtration and concentration of the filtrate in vacuo gave (3S,4S)-4-(1-iodomethylethenyl)-3-(1-(R)-benzyloxycarbonyloxyethyl)-1-di-(p-anisyl)methyl-2-azetidinone.

IR $\nu_{max}^{neat}$ (cm$^1$): 1755, 1615, 1510, 1385, 1250, 1180, 1030.

NMR δ (CDCl$_3$): 1.43 (3H, d, J=6.5 Hz), 3.34 (1H, dd, J=2.5 and 6.5 Hz), 3.74 (6H, s), 4.32 (1H, d, J=2.5 Hz), 5.18 (2H, AB$_q$, J=9.5 Hz), 5.54 (1H, s), 7.39 (5H, s).

EXAMPLE 9-(2)

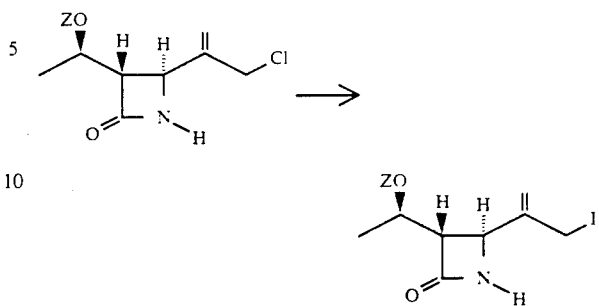

By the similar procedure to that described in Example 9-(1), there was obtained (3S,4S)-4-(1-iodomethylethenyl)-3-(1-(R)-benzyloxycarbonyloxyethyl)-2-azetidinone from the corresponding (3S,4S)-4-(1-chloromethylethenyl) derivative.

IR $\nu_{max}^{neat}$ (cm$^1$): 1740, 1450, 1380, 1260, 1160, 1140.

NMR δ (CDCl$_3$): 1.47 (3H, d, J=6.5 Hz), 3.09 (1H, dd, J=2 and 9 Hz), 3.90 (2H, s), 4.38 (1H, d, J=2 Hz), 5.19 (2H, s), 7.36 (5H, s).

EXAMPLE 10-(1)

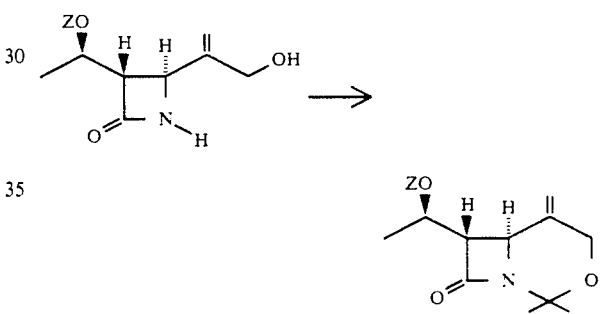

A solution of (3S,4S)-4-(1-hydroxymethylethenyl)-3-(1-(R)-benzyloxycarbonyloxyethyl)-2-azetidinone (3.7 g) and 2,2-dimethoxypropane (1.45 g) in dry dichloromethane (26 ml) was treated with boron trifluoride-etherate (0.14 ml) at room temperature for 1.5 hours. The reaction mixture was washed successively with saturated sodium bicarbonate (15 and water (20 ml×2), and dried over anhydrous sodium sulfate. Filtration and concentration of the filtrate in vacuo gave an oily residue, which was purified by silica gel chromatography to yield (6S,7S)-8-oxo-2,2-dimethyl-5-methylidene-7-(1-(R)-benzyloxycarbonyloxyethyl)-3-oxa-1-azabicyclo[4.2.0]octane.

IR $\nu_{max}^{neat}$ (cm$^1$): 1755, 1455, 1380, 1355, 1260, 1140, 1040, 910.

NMR δ (CDCl$_3$): 1.43 (3H,s), 1.47 (3H, d, J=6.5 Hz), 1.70 (3H, s), 3.22 (1H, dd, J =2 and 8 Hz), 5.17 (2H, s), 7.37 (5H, s).

EXAMPLE 10-(2)

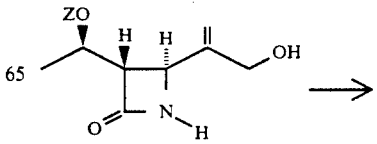

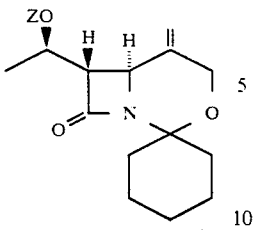

Following the procedure as described in Example but replacing 2,2-dimethoxypropane by 1,1-dimethoxycyclohexane, there was obtained (6S,7S)-spiro[cyclohexane-2,2-(8-oxo-5-methylidene-7-(1-(R)-benzyloxycarbonyloxyethyl)-3-oxa-1-azabicyclo[4.2.0]octane)].

IR $\nu_{max}^{neat}$ (cm$^1$): 1750, 1425, 1250, 1140, 1040, 900.

NMR δ (CDCl$_3$): 1.47 (3H,d, J=6.0 Hz), 1.74 (10H, bs), 3.21 (1H, dd, J=2 and 8 Hz), 5.16 (2H, s), 7.36 (5H, s).

EXAMPLE 11-(1)

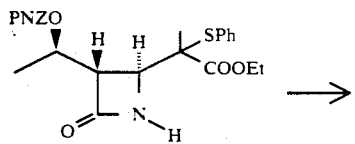

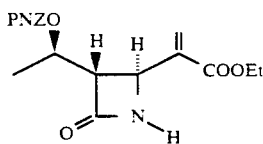

A solution of (3S,4S)-4-(1-phenylthio-1-ethoxycarbonylethyl)-3-(1-(R)-p-nitrobenzyloxycarbonyloxyethyl)-2-azetidinone (2.0 g) in dry dichloromethane (50 ml) was treated with m-chloroperbenzoic acid (0.69 g) for 3 hours while ice-cooling. The reaction mixture was washed successively with a saturated sodium bicarbonate solution and brine, and dried over anhydrous sodium sulfate. Filtration and concentration of the filtrate in vacuo gave an oily residue which was dissolved in toluene (18 ml). The toluene solution was stirred under reflux for 1 hour and concentrated in vacuo. An oily residue was purified by silica gel chromatography to yield (3S,4S)-4-(1-ethoxycarbonylethenyl)-3-(1-(R)-p-nitrobenzyloxycarbonyloxyethyl)-2-azetidinone.

IR $\nu_{max}^{neat}$ (cm$^1$): 1750, 1720, 1520, 1375, 1345, 1260, 1145, 850.

NMR δ (CDCl$_3$): 1.30 (3H, t, J=7.0 Hz), 1.48 (3H, d, J=6.5 Hz), 3.18 (1H, dd, J=2 and 7.0 Hz), 4.22 (2H, q, J =7.0 Hz), 4.55 (1H, bd, J=2.0 Hz), 5.26 (2H, s), 5.88 (1H, s), 6.34 (1H, s), 7.56 (2H, d, J=8.8 Hz), 8.21 (2H, d, J=8.8 Hz).

EXAMPLE 11-(2)

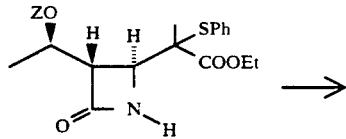

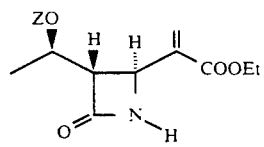

Following the procedure as described in Example 11-(1) but replacing the starting material by (3S,4S)-4-(1-phenylthio-1-ethoxycarbonylethyl)-3-(1-(R)-benzyloxycarbonyloxyethyl)-2-azetidinone, there was obtained (3S,4S)-4-(1-ethoxycarbonyethenyl)-3-(1-(R)-benzyloxycarbonyloxyethyl)-2-azetidinone. This compound was also obtained when (3S,4S)-4-(1-carboxyethenyl)-3-(1-(R)-benzyloxycarbonyloxyethyl)-2-azetidinone was treated with ethyl iodide in the presence of anhydrous potassium carbonate.

NMR δ (CDCl$_3$): 1.27 (3H, t, J=7 Hz), 1.45 (3H, d, J=6 Hz), 3.18 (1H, dd, J=2.5 and 7 Hz), 4.20 (2H, q, J=7 Hz), 4.53 (1H, br, s) 5.17 (2H, s), 5.22 (1H, m), 5.86 (1H, s), 6.31 (1H, s), 6.53 (1H, br, s), 7.39 (5H, s).

EXAMPLE 11-(3)

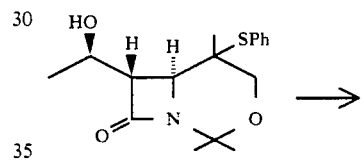

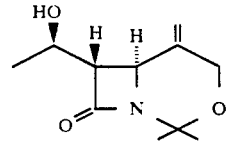

Following the procedure as described in Example 11-(1) but replacing the starting material by (6S,7S)-8-oxo-2,2-dimethyl-5-methyl-5-phenylthio-7-(1-(R)-hydroxyethyl)-3-oxa-1-azabicyclo[4,2,0]octane, there was obtained (6S,7S)-8-oxo-2,2-dimethyl-5-methylidene-7-(1-(R)-hydroxyethyl)-3-oxa-1-azabicyclo[4,2,0]octane.

NMR δ (CDCl$_3$): 1.34 (3H, d, J=6.4 Hz), 1.46 (3H, s), 1.73 (3H, s), 2.04 (1H, br, s), 3.10 (1H, dd, J=1.9 and 5.4 Hz), 4.98 (1H, d, J=1.5 Hz), 5.10 (1H, d, J=2.0 Hz).

EXAMPLE 11-(4)

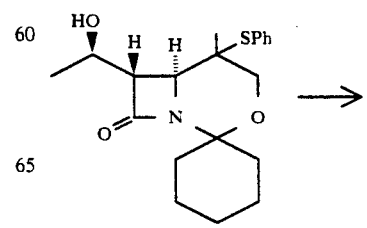

-continued

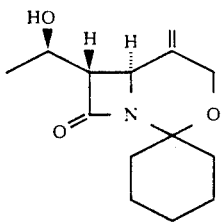

Following the procedure as described in Example 11-(1) but replacing the starting material by (6S,7S)-spiro[cyclohexane-2,2-(8-oxo-5-methyl-5-phenylthio-7-(1-(R)-hydroxyethyl)-3-oxa-1-azabicyclo(4,2,0) octane], there was obtained (6S,7S)-spiro[cyclohexane-2,2-(8-oxo-5-methylidene-7-(1-(R)-hydroxyethyl)-3-oxa-1-azabicyclo[4,2,0]-octane].

NMR δ (CDCl$_3$): 1.35 (3H, d, J=6.4 Hz), 1.48–1.76 (10H, m), 3.10 (1H, dd, J=2.0 and 5.5 Hz), 4.97 (1H, d, J=1.3 Hz), 5.11 (1H, d, J=1.3 Hz).

EXAMPLE 12-(1)

In the same manner as in Example 2, there was obtained the following compound:

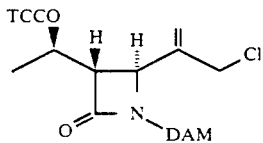

IR $\nu_{max}^{neat}$ (cm$^{-1}$): 1760, 1615, 1512, 1382, 1250, 1178, 1130, 820.

NMR δ (CDCl$_3$): 1.46 (3H, d, J=6.5 Hz), 3.35 (1H, dd, J=2.5 and 6 Hz), 3.80 (6H, s), 4.30 (1H, d, J=2.5 Hz), 4.80 (2H, AB$_q$, J=12 Hz), 5.27 (1H, s), 5.33 (1H, s), 5.60 (1H, s).

EXAMPLE 12-(2)

In the same manner as in Example 3-(1), there was obtained the following compound:

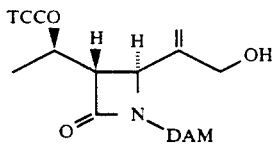

IR $\nu_{max}^{neat}$ (cm$^{-1}$) 3430, 1755, 1610, 1510, 1380, 1245, 1180, 1030, 820.

NMR δ (CDCl$_3$) 1.45 (3H, d, J=6.5 Hz), 3.29 (1H, dd, J=2.5 and 6 Hz), 3.79 (6H, s), 4.24 (1H, d, J=2.5 Hz), 4.79 (2H, AB$_q$, J=12 Hz), 5.59 (1H, s).

EXAMPLE 12-(3)

In the same manner as in Example 5-(1), there was obtained the following compound:

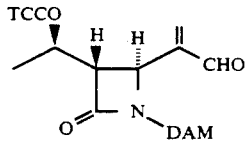

IR $\nu_{max}^{neat}$ (cm$^{-1}$): 1765, 1695, 1620, 1520, 1388, 1250, 1182, 1035, 825.

NMR δ (CDCl$_3$): 1.42 (3H, d, J=6.5 Hz), 3.22 (1H, dd, J=2.5 and 6 Hz), 3.77 (3H, s), 3.78 (3H, s), 4.61 (1H, d, J=2.5 Hz), 4.82 (2H, AB$_q$, J =12 Hz), 5.24 (1H, m), 5.67 (1H, s), 5.92 (1H, s), 6.20 (1H, s), 9.36 (1H, s).

EXAMPLE 12-(4)

In the same manner as in Example 9-(1), there was obtained the following compound:

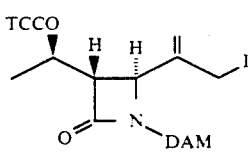

IR $\nu_{max}^{neat}$ (cm$^{-1}$): 1520, 1385, 1250, 1180, 1030, 820.

NMR δ (CDCl$_3$): 1.47 (3H, d, J=6.5 Hz), 3.40 (1H, dd, J=2.5 and 6.5 Hz), 3.69 (2H, s), 3.79 (6H, s), 4.31 (1H, d, J=2.5 Hz), 4.80 (2H, AB$_q$, J =12 Hz), 5.20 (1H, s), 5.39 (1H, s), 5.57 (1H, s).

EXAMPLE 13

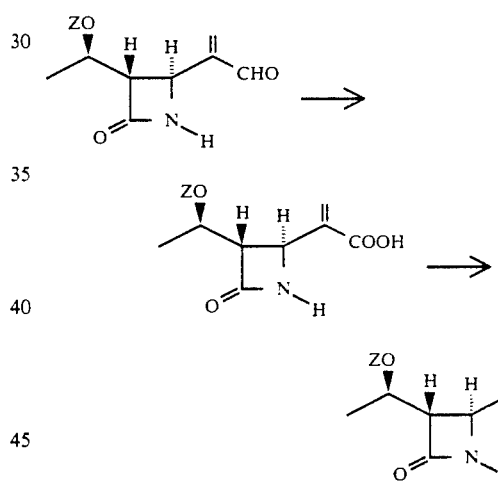

(3S,4S)-4-(1-Carboxyethenyl)-3-(1-(R)-benzyloxycarbonyloxyethyl)-2-azetidinone (37 g), which was prepared from (3S,4S)-4-(1-formylethenyl)-3-(1-(R)-benzyloxycarbonyloxyethyl)-2-azetidinone in the similar procedure to Example 6, was dissolved in methanol and then diluted with diethyl ether. A solution of diazomethane in diethyl ether was added dropwise thereto with ice-cooling, and the resultant mixture was stirred for 0.5 hour. After removal of excess diazomethane, the reaction mixture was concentrated in vacuo to give (3S,4S)-4-(1-methoxycarbonylethenl)-3-(1-(R)-benzyloxycarbonyloxyethyl)-2-azetidinone.

IR $\nu_{max}^{neat}$ (cm$^{-1}$): 3300, 1750, 1630, 1440, 1380, 1332, 1260, 1145, 750, 695.

NMR δ (CDCl$_3$): 1.45 (3H, d, J=6.5 Hz), 3.15 (1H, dd, J=2 and 7 Hz), 3.74 (3H, s), 4.52 (1H, d, J=2 Hz), 5.17 (2H, s), 5.87 (1H, s), 6.32 (1H, s), 6.58 (1H, bs), 7.36 (5H, s).

EXAMPLE 14

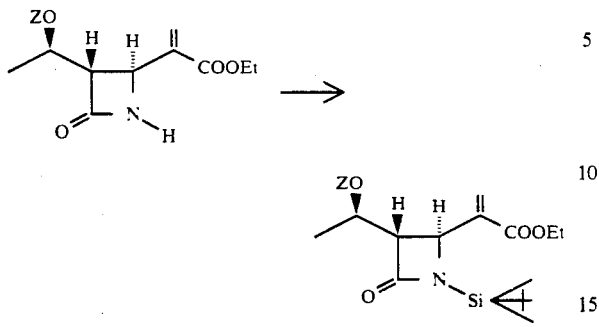

t-Butyldimethylchlorosilane (0.96 g) was added to an ice-cold, stirred solution of (3S,4S)-4-(1-ethoxycarbonylethenyl)-3-(1-(R)-benzyloxycarbonyloxyethyl)-2-azetidinone (1.0 g) and triethylamine (0.88 g) in dry dimethylformamide (12 ml), followed by stirring at room temperature for 15 hours. The reaction mixture was diluted with ethyl acetate (50 ml), washed with brine and dried over anhydrous sodium sulfate. Filtration and concentration of the filtrate in vacuo gave an oily residue, which was purified by silica gel chromatography to obtain (3S,4S)-4-(1-ethoxycarbonylethenyl)-3-(1-(R)-benzyloxycarbonylethyl)-1-t-butyldimethylsilyl-2-azetidinone.

NMR δ (CDCl$_3$): 0.04 (3H, s), 0.26 (3H, s), 0.95 (9H, s), 1.30 (3H, t, J=7.25 Hz), 1.41 (3H, d, J=6.5 Hz), 3.23 (1H, dd, J=2.5 and 6.5 Hz), 4.23 (2H, q, J=7.25 Hz), 5.16 (2H, s), 5.16 (1H, m), 5.86 (1H, s), 6.30 (1H, s), 7.35 (5H, s).

EXAMPLE 15-(1)

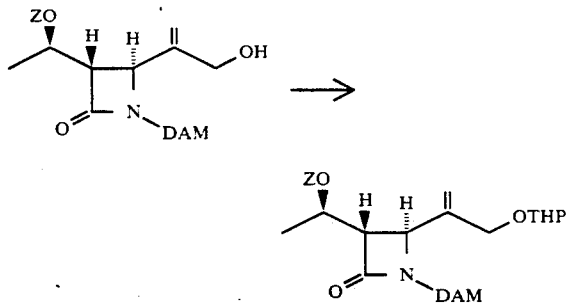

A solution of (3S,4S)-4-(1-hydroxymethylethenyl)-3-(1-(R)-benzyloxycarbonyloxyethyl)-1-di(p-anisyl)methyl-2-azetidinone (106 mg) and dihydropyran (25 mg) in dry dichloromethane (1 ml) was treated with p-toluenesulfonic acid (1 mg) at room temperature for 50 minutes. The reaction mixture was diluted with ethyl acetate, washed with brine and dried over anhydrous sodium sulfate. Filtration and concentration of the filtrate in vacuo gave an oily residue, which was purified by thin-layer chromatography (SiO$_2$) to yield (3S,4S)-4-(1-tetrahydropyranyloxymethylethenyl)-3-(1-(R)-benzyloxycarbonyloxyethyl)-1-di(p-anisyl)methyl-2-azetidinone.

NMR δ (CDCl$_3$): 1.39 (3H, d, J=6.2 Hz), 1.58 (6H, m), 3.72 (3H, s), 3.73 (3H, s), 5.18 (2H, s), 5.53 (1H, br, s), 7.39 (5H, s).

EXAMPLE 15-(2)

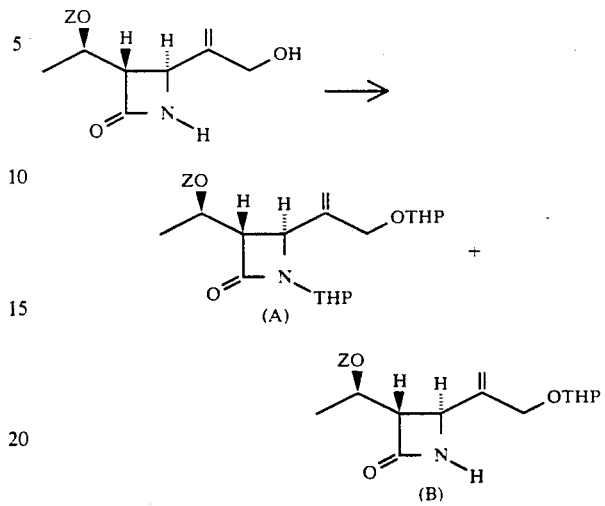

Following the procedure as described in Example 15-(1) but replacing the starting material by (3S,4S)-4-(1-hydroxymethylethenyl)-3-(1-(R)-benzyloxycarbonyloxyethyl)-2-azetidinone, (3S,4S)-4-(1-tetrahydropyranyloxymethylethenyl)-3-(1-(R)-benzyloxycarbonyloxyethyl)-1-tetrahydropyranyl-2-azetidinone (Compound A) and (3S,4S)-4-(1-tetrahydropyranyloxymethylethenyl)-3-(1-(R)-benzyloxycarbonyloxyethyl)-2-azetidinone (Compound B) were obtained.

Compound (A):

NMR δ (CDCl$_3$) 1.38–1.84 (15H, m), 3.22–4.34 (9H, m), 4.61 (1H, m), 4.97 (2H, m), 5.06 (1H, m), 5.15 (2H, s), 5.26 (1H, m), 7.36 (5H, s).

Compound (B):

NMR δ (CDCl$_3$): 1.44 (3H, d, J=6.4 Hz), 1.58 (6H, m), 4.02 (1H, s), 4.57 (1H, br, s), 5.08 (1H, m), 5.15 (2H, s), 5.21 (2H, br, s), 7.36 (5H, s).

EXAMPLE 16

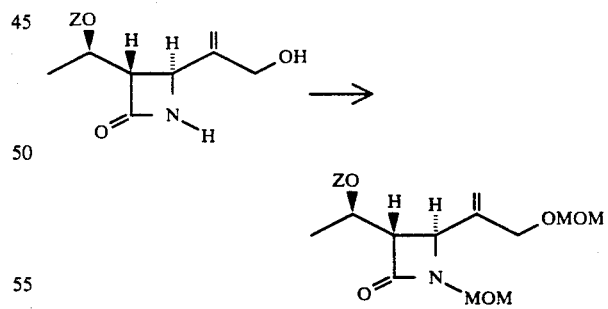

A solution of (3S,4S)-4-(1-hydroxymethylethenyl)-3-(1-(R)-benzyloxycarbonyloxyethyl)-2-azetidinone (305 mg) and dimethoxymethane (5.2 ml) in dry chloroform (5.2 ml) was treated with phosphorus pentoxide (2.68 g) at room temperature for 3 hours. The reaction mixture was diluted with dichloromethane (80 ml), washed successively with 10% sodium bicarbonate and water and dried over anhydrous sodium sulfate. Filtration and concentration of the filtrate in vacuo gave an oily residue, which was purified by thin-layer chromatography (SiO$_2$) to yield (3S,4S)-4-(1-methoxymethoxymethylethenyl)-3-(1-(R)-benzyloxycarbonyloxyethyl)-1-methoxymethyl-2-azetidinone.

NMR δ (CDCl₃): 1.43 (3H, d, J=6.5 Hz), 3.32 (3H, s), 3.33 (3H, s), 4.04 (2H, s), 4.58 (2H, d, J=1.1 Hz), 4.62 (1H, d, J=2.2 Hz), 5.15 (2H, s), 5.23 (1H, s), 5.29 (1H, s), 7.34 (5H, s).

REFERENCE EXAMPLE 1-(1)

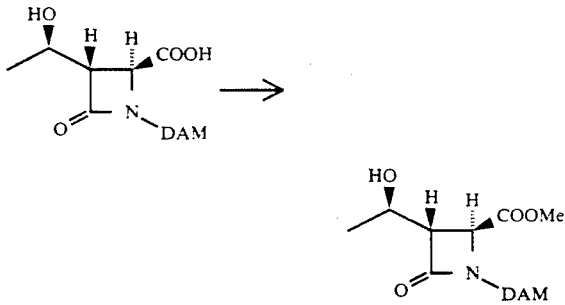

To a solution of (3S,4S)-4-carboxy-3-(1-(R)-hydroxyethyl)-1-di(p-anisyl)methyl-2-azetidinone (34 g) in methanol (310 ml) was added 98% sulfuric acid (2.9 g), and the resultant mixture was heated at 65° C. for 3 hours, cooled down to 40° C., neutralized with 8% sodium hydroxide (15 ml) and concentrated to make a one third volume. The concentrate was diluted with 1,2-dichloroethane (105 ml) and washed with water. The aqueous layer was separated from the organic layer and extracted with 1,2-dichloroethane (105 ml). The extracts and the organic layer were combined together, washed with water and dried over anhydrous sodium sulfate. Filtration and concentration of the filtrate in vacuo gave (3S,4S)-4-methoxycarbonyl-3-(1-(R)-hydroxyethyl)-1-di(p-anisyl)methyl-2-azetidinone. m.p., 102°–104° C.

REFERENCE EXAMPLE 1-(2)

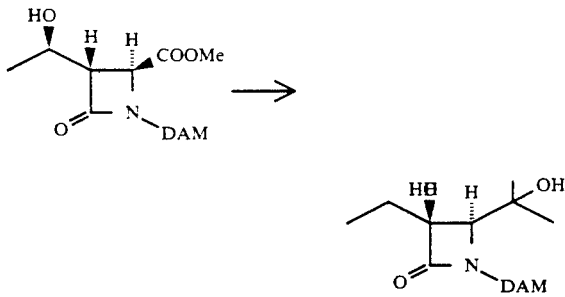

To a solution of (3S,4S)-4-methoxycarbonyl-3-(1-(R)-hydroxyethyl)-1-di(p-anisyl)methyl-2-azetidinone (32.5 g) in dry tetrahydrofuran (310 ml) was added dropwise a 1M suspension of methyl magnesium bromide in tetrahydrofuran (370 g) at 0°–5° C., and the suspension was stirred at the same temperature as above for 1 hour. 20% Hydrochloric acid (350 ml) was poured into the suspension at 20°–25° C., and the resultant mixture was stirred for 1 hour, followed by extraction with ethyl acetate (110 ml). The aqueous layer was reextracted with ethyl acetate (110 ml). The ethyl acetate extracts were combined together, washed successively with brine, saturated sodium bicarbonate and water and dried over anhydrous sodium sulfate. Filtration and concentration of the filtrate in vacuo gave (3S,4S)-4-(1-hydroxy-1-methylethyl)-3-(1-(R)-hydroxyethyl)-1-di(p-anisyl)methyl-2-azetidinone. m.p., 154°–156° C.

REFERENCE EXAMPLE 1-(3)

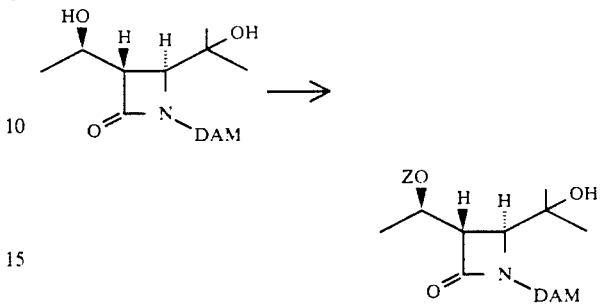

(3S,4S)-4-(1-Hydroxy-1-methylethyl)-3-(1-(R)-hydroxyethyl)-1-di(p-anisyl)methyl-2-azetidinone (26 g) and 4-dimethylaminopyridine (16 g) were dissolved in dry dichloromethane (200 ml). Benzyl chloroformate (20 g) was added dropwise thereto over a period of 1 hour with ice-cooling, and the resultant mixture was stirred for 2 hours and warmed to room temperature, followed by stirring at the same temperature as above for 10 hours. 5% Hydrochloric acid (100 ml) was poured into the reaction mixture with ice-cooling, and the resulting mixture was stirred for 0.5 hour and allowed to stand. The organic layer was washed successively with water, a saturated sodium bicarbonate solution and brine and dried over anhydrous sodium sulfate. Filtration and concentration of the filtrate in vacuo gave (3S,4S)-4-(1-hydroxy-1-methylethyl)-3-(1-(R)-benzyloxycarbonyloxyethyl)-1-di(p-anisyl)methyl-2-azetidinone.

IR $ν_{max}^{neat}$(cm⁻¹) 3450, 1750, 1615, 1515, 1250, 1180, 1030.

NMR δ (CDCl₃) 1.13 (6H, s), 1.38 (3H, d, J=6 Hz), 3.70 (3H, s), 3.75 (3H, s), 5.10 (2H, s), 5.55 (1H, bs), 7.29 (5H, s).

REFERENCE EXAMPLE 1-(4)

Following the procedure as described in Reference Example 1-(3), the following compounds were obtained when (3S,4S)-4-(1-hydroxy-1-methylethyl)-3-(1-(R)-hydroxyethyl)-1-di(p-anisyl)methyl-2-azetidinone was treated with R₄Cl:

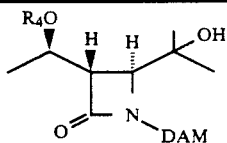

| No. | R₄ | Spectra data | |
|---|---|---|---|
| 1 | TCC | IR $ν_{max}^{neat}$ (cm⁻¹): | 3450, 1750, 1610, 1582, 1510, 1460, 1378, 1245, 1170, 1030, 820. |
| | | NMR δ (CDCl₃): | 1.18(3H, s), 1.21(3H, s), 1.44(3H, d, J=6.5Hz), 3.01(1H, dd, J=2 and 7.5 Hz), 3.64(1H, d, J=2Hz), 3.78(3H, s), 3.79(3H, s), 4.76(2H, AB_q, J=12Hz), 5.07(1H, m), 5.64(1H, s). |
| 2 | PNZ | IR $ν_{max}^{neat}$ (cm⁻¹): | 1750, 1610, 1517, 1345, 1250, 1172, 1030, 850. |
| | | NMR δ (CDCl₃): | 1.16(6H, s), 1.39(3H, d, J=6.5Hz), 2.96(1H, dd, |

-continued

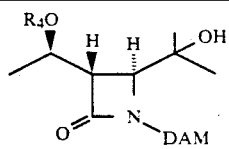

| No. | R₄ | Spectra data |
|---|---|---|
| | | J=2 and 7Hz), 3.63(1H, d, J=2Hz), 3.70(3H, s), 3.76(3H, s), 5.19(2H, s), 5.57(1H, s). |

REFERENCE EXAMPLE 2-(1)

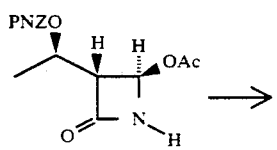

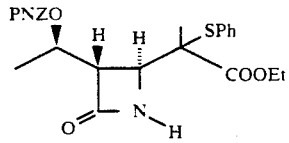

To a solution of (3R,4R)-4-acetoxy-3-(1-(R)-p-nitrobenzyloxycarbonyloxyethyl)-2-azetidinone (1.76 g) in dry dichloromethane (30 ml) was added at room temperature ethyl-alpha-phenylthiopropionate trimethylsilylketeneacetal (5.64 g), which was prepared from ethyl-alpha-phenylthiopropionate, chlorotrimethylsilane and lithium diisopropylamide at room temperature, under nitrogen atmosphere. After addition of zinc iodide (1.6 g), the mixture was stirred at 35° C. for 2 hours. The reaction mixture was diluted with dichloromethane (200 ml), and a saturated sodium bicarbonate solution (100 ml) was added thereto. The resulting mixture was stirred for 15 minutes, followed by filtration to remove insoluble materials. The organic layer was washed with brine and dried over anhydrous sodium sulfate Filtration and concentration of the filtrate in vacuo gave an oily residue, which was purified by silica gel chromatography to yield (3S,4S)-4-(1-phenylthio-1-ethoxycarbonylethyl)-3-(1-(R)-p-nitrobenzyloxycarbonyloxyethyl)-2-azetidinone.

IR $\nu_{max}^{neat}$ (cm⁻¹): 1750, 1720, 1605, 1520, 1375, 1340, 1250, 1140, 840, 745.

NMR δ (CDCl₃): 3.41 (1H, m), 5.20 (2H, s), 6.14 (½H, bs), 6.28 (½H, bs).

REFERENCE EXAMPLE 2-(2)

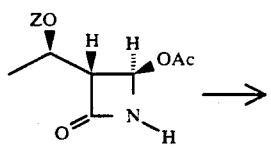

-continued

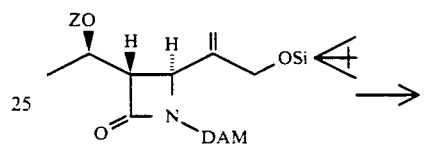

Following the procedure as described in Reference Example 2-(1) but replacing the starting material by (3R,4R)-4-acetoxy-3-(1-(R)-benzyloxycarbonyloxyethyl)-2-azetidinone, there was obtained (3S,4S)-4-(1-phenylthio-1-ethoxycarbonylethyl)- 3-(1-(R)-benzyloxycarbonyloxyethyl)-2-azetidinone.

IR $\nu_{max}^{neat}$ (cm⁻¹): 1750, 1380, 1255, 1140, 1015, 750.

NMR δ (CDCl₃): 3.31 (½H, dd, J=2.2 and 7.5 Hz), 3.45 (½H, br, d, J=8.4 Hz), 5.12 (2H, s), 6.07 (½H, br, s), 6.21 (½H, br, s), 7.31 (5/2H, s), 7.33 (5.2H, s).

REFERENCE EXAMPLE 3-(1)

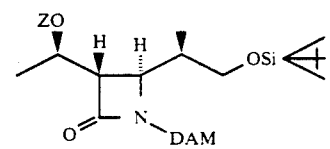

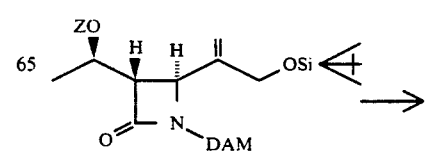

To a solution f (3S,4S)-4-(1-t-butyldimethylsilyloxymethylethenyl)-3-(1-(R)-benzyloxycarbonyloxyethyl)-1-di(p-anisyl)methyl-2-azetidinone (20 g) in acetonitrile (200 ml) were added 5% platinum on activated carbon (4.0 g) and water (4 ml) under nitrogen atmosphere. The mixture was stirred at 10° C. in a hydrogen gas flow until 2.2 equivalents of hydrogen had been taken up. The catalyst was removed by filtration and washed with ethyl acetate. The filtrate and the washings were combined together and concentrated in vacuo to give (3S,4S)-4-(1-t-butyldimethylsilyloxymethylethyl)-3-(1-(R)-benzyloxycarbonyloxyethyl)-1-di-(p-anisyl)methyl-2-azetidinone as an oil.

High performance liquid chromatography (HPLC) [Lichrosorb® RP-18], eluting with 85% acetonitrile/water (1 ml/min) and NMR spectra indicated that this product was a mixture of 4-(1-(R)-t-butyldimethylsilyloxyethyl) compound and the corresponding (S)-compound in a ratio of 7.7:1. The above mixture was recrystallized from a mixture of n-hexane and ethyl acetate (10 : 1) to yield the (R)-compound. m.p., 78°-81° C.

NMR δ (CDCl₃): 0.01 (6H, s), 0.87 (9H, s), 1.40 (3H, d, J=6 Hz), 3.31 (1H, dd, J =2.2 and 7.0 Hz), 3.44 (2H, d, J =5.3 Hz), 3.73 (3H, s), 3.76 (3H, s), 5.07 (1H, m), 5.17 (2H, s), 7.38 (5H, s).

REFERENCE EXAMPLE 3-(2)

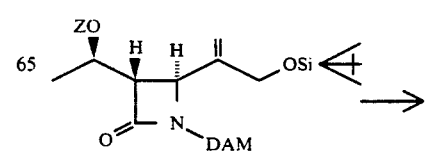

-continued

The (R)-compound was preferentially obtained by the same procedure as described in Reference Example 3-(1) or 3-(2) but changing the catalysts and solvents as shown in Table 1.

TABLE 1

| No. | Starting material (g) | Catalyst (g) | Solvent (ml) | Reaction condition | | Yield (%) | Ratio* (R/S) |
|---|---|---|---|---|---|---|---|
| | | | | Temperature (°C.) | Time (hr) | | |
| 1 | 1.0 | 5% Pt/C (0.2) | CH₃CN (10) | 10 | 4.5 | 84 | 4.6 |
| 2 | 4.0 | 5% Pt/C (0.8) | CH₃CN (40) H₂O (1.5) Et₃N (0.06) | 20 | 8.0 | 100 | 6.2 |
| 3 | 0.5 | 5% Pt/C (0.1) | DMF (5) H₂O (0.1) | 20 | 3.0 | 93 | 5.3 |
| 4 | 10.0 | PtO₂ (0.2) | CH₃CN (50) | 25 | 18 | 92 | 7.8 |

Note:
*The production proportion of the (R)-compound and the (S)-compound was calculated from HPLC

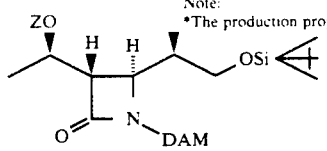

REFERENCE EXAMPLE 4-(1)

A solution of (3S,4S)-4-(1-t-butyldimethylsilyloxymethylethenyl)-3-(1-(R)-benzyloxycarbonyloxyethyl)-1-di(p-anisyl)methyl-2-azetidinone (1.0 g) and triethylamine (0.06 ml) in ethyl acetate (50 ml) was hydrogenated under hydrogen atmosphere in the presence of platinum dioxide (0.05 g) at 0°–5° C. for 2 hours. After removal of the catalyst, the filtrate was washed successively with 2N hydrochloric acid, brine, 5% sodium bicarbonate solution and brine and dried over anhydrous magnesium sulfate. Filtration and concentration of the filtrate in vacuo gave (3S,4S)-4-(1-t-butyldimethylsilyloxymethylethyl)-3-(1-(R)-benzyloxycarbonyloxyethyl)-1-di(p-anisyl)methyl-2-azetidinone.

The weight proportion of the (R)-compound and the (S)-compound in this product was confirmed to be 5.4:1 by HPLC.

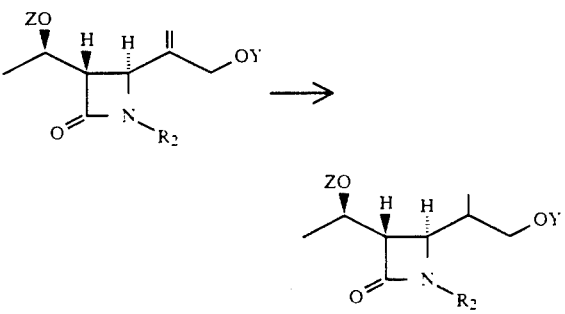

Following the procedure as described in Reference Example 3-(1) or 3-(2) but using platinum oxide as the catalyst, the compounds as shown in Table 2 were obtained.

TABLE 2

| No. | Starting material | | | Reaction condition | | | | | Objective compound |
|---|---|---|---|---|---|---|---|---|---|
| | Y | R₂ | Amount | PtO₂ (mg) | Solvent (ml) | Temp. (°C.) | Time (hr) | Yield (%) | Ratio* (R/S) | Spectra data |
| 1 | Si⟨ | Si⟨ | 10.64 (g) | 220 | EtOH (106) | 0–5 | 6 | 73 | 1.22 | IR ν$_{max}^{neat}$ (cm⁻¹): 1745, 1462, 1380, 1260, 1090, 837. |
| | | | | | | | | | | NMR δ (CDCl₃) of (R)-compound: 0.01(6H, s), 0.13(3H, s), 0.25 (3H, s), 0.85(9H, s), 0.93(9H, s), 0.93(3H, d, J=6.8Hz), 1.37(3H, d, J=6.4Hz), 3.37 (1H, dd, J=2.4 and 7.0Hz), 3.58(3H, m), 5.00(1H, m), 5.10 (2H, s), 7.31(5H, s). |
| | | | | | | | | | | NMR δ (CDCl₃) of (S)-compound: 0.01(3H, s), 0.03(3H, s), 0.18 (3H, s), 0.29(3H, s), 0.88(3H, d, J=6.8Hz), 0.88(9H, s), 0.96(9H, s), 1.40(3H, d, J= 6.4Hz), 3.08(1H, dd, J=2.7 and 6.6Hz), 3.84(1H, t, J= 2.7Hz), 5.04(1H, m), 5.13(2H, s), 7.35(5H, s). |
| 2 | THP | THP | 35 (mg) | 3.5 | MeCN (3.5) | 0–5 | 3 | 100 | 2.0 | NMR δ (CDCl₃) of the mixture of (R)- and (S)-compound: 0.83–1.09(3H, m), 1.26–1.66 (15H, m), 3.44–4.05(9H, m), 4.53(1H, br. s), 4.94(1H, m), 5.05(1H, m), 5.14(2H, s), 7.36 (5H, s). |
| 3 | MOM | MOM | 20 (mg) | 2.0 | MeCN (2.0) | 0–5 | 3 | 100 | 1.30 | NMR δ (CDCl₃) of (R)-compound: 1.03(3H, d, J=6.8Hz), 1.44 (3H, d, J=6.5Hz), 3.33(6H, s), 4.55(4H, s), 5.15(2H, s), |

TABLE 2-continued

| No. | Starting material Y | R₂ | Amount | Reaction condition PtO₂ (mg) | Solvent (ml) | Temp. (°C.) | Time (hr) | Yield (%) | Ratio* (R/S) | Objective compound Spectra data |
|---|---|---|---|---|---|---|---|---|---|---|
| 4 | MOM | MOM | 20 (mg) | 2.0 | EtOAc (2.0) Et₃N (0.98 mg) | 0-5 | 3 | 75 | 1.15 | 7.35(5H, s). NMR δ (CDCl₃) of (S)-compound: 0.95(3H, d, J=7.0Hz), 1.44 (3H, d, J=6.5Hz), 3.33(6H, s), 4.55(4H, s), 7.35(5H, s). |
| 5 | SiMePh₂ | DAM | 49 (mg) | 4.9 | MeCN (4.9) | 0-5 | 1.5 | 90 | 3.33 | NMR δ (CDCl₃) of the mixture of (R)- and (S)-compound: 0.58(3H, s), 0.66(3H, s), 0.71 (3H, d, J=6.8Hz), 0.86(3H, d, J=6.8Hz), 1.34(3H, d, J= 6.4Hz), 3.52(2H, d, J=1.3Hz), 5.12(2H, d, J=1.3Hz), 5.44(1H, s), 6.73(4H, dd, J= 2.6 and 8.8Hz), 7.35(5H, s). |
| 6 | THP | DAM | 25 (mg) | 2.5 | MeCN (2.5) | 0-5 | 4 | 44 | 3.0 | NMR δ (CDCl₃) of (R)-compound: 0.92(3H, d, J=7.0Hz), 1.40 (3H, d, J=6.2Hz), 3.72(3H, s), 3.75(3H, s), 5.16(2H, s), 5.59(1H, br, s), 7.37(5H, s). NMR δ (CDCl₃) of (S)-compound: 0.89(3H, d, J=6.8Hz), 1.40 (3H, d, J=6.2Hz). |
| 7 | H | DAM | 50 (mg) | 5 | MeCN (5.0) | 0-5 | 3 | 86 | 1.4 | Identical to the sample of Reference Example 6-(1) |
| 8 | THP | H | 25 (mg) | 2.5 | MeCN (2.5) | 0-5 | 3 | 92 | 0.77 | NMR δ (CDCl₃) of (R)-compound: 0.97(3H, d, J=6.4Hz), 1.01 (3H, d, J=6.4Hz), 4.50(1H, br, s), 5.09(1H, m), 5.14 (2H, s), 7.36(5H, s). NMR δ (CDCl₃) of (S)-compound: 0.83(3H, d, J=6.4Hz), 0.85 (3H, d, J=6.4Hz). |

Note:
*The production proportion of the (R)-compound and the (S)-compound was calculated from the NMR data.

REFERENCE EXAMPLE 4-(2)

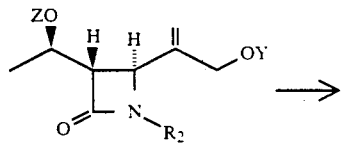

→

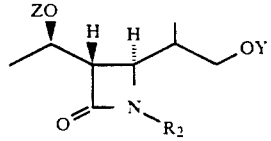

In the similar procedure to the one as described in Reference Example 3-(1), 3-(2) or 4-(1), there were obtained the compounds as shown in Table 3.

TABLE 3

| No. | Starting material Y | R₂ | Amount (mg) | Reaction condition Catalyst (mg) | Solvent (ml) | Temp. (°C.) | Time (hr) | Yield (%) | Ratio* (R/S) | Objective compound Spectra data |
|---|---|---|---|---|---|---|---|---|---|---|
| 1 | Si⦅ | DAM | 50 | PtO₂ (25) | EtOH (2.5) | room temp. | 0.5 | 100 | 3.0 | NMR δ (CDCl₃) of (R)-compound: 0.07(6H, s), 0.87(9H, s), 0.87 (3H, d, J=7.0Hz), 1.27(3H, d, J=6.0Hz), 3.07(1H, dd, J= 2.2 and 7.0Hz), 3.79(6H, s), 5.62(1H, br, s). |
| 2 | Si⦅ | DAM | 50 | 10% Pd/C (25) | MeCN (2.5) | 0-5 | 1 | 73 | 2.6 | |
| 3 | Si⦅ | Si⦅ | 31 | PtO₂ (15) | EtOH (2) | room temp. | 3 | 100 | 2.2 | NMR δ (CDCl₃) of (R)-compound: 0.01(6H, s), 0.15(3H, s), 0.24 (3H, s), 0.85(9H, s), 0.93(9H, s), 0.98(3H, d, J=7.0Hz), 1.23(3H, d, J=6.4Hz), 2.5 2H, br, d, J=4.5Hz), 3.15 (1H, dd, J=2.5 and 6.0Hz), 3.57(1H, dd, J=2.5 and 4.2 Hz), 4.04(1H, m). NMR δ (CDCl₃) of (S)-compound: 0.04(6H, s), 0.13(3H, s), 0.27 (3H, s), 0.82(3H, d, J=7.0 Hz), 0.87(9H, s), 0.93(9H, s), 1.28(3H, d, J=6.4Hz), 2.92 (1H, dd, J=2.5 and 8.5Hz). |
| 4 | THP | DAM | 20 | PtO₂ | EtOH | room | 2.5 | 65 | 2.5 | NMR δ (CDCl₃ of (R)-compound: |

TABLE 3-continued

| | Starting material | | | Reaction condition | | | | | Objective compound |
|---|---|---|---|---|---|---|---|---|---|
| No. | Y | R$_2$ | Amount (mg) | Catalyst (mg) | Solvent (ml) | Temp. (°C.) | Time (hr) | Yield (%) | Ratio* (R/S) | Spectra data |
| | | | | (5) | (2.0) 0.01M KH$_2$PO$_4$ buffer (0.2) | temp. | | | | 0.95(3H, d, J=7Hz), 1.26 (3H, d, J=6.0Hz), 3.79(6H, s), 6.88(1H, br, s). NMR δ (CDCl$_3$) of (S)-compound: 0.78(3H, d, J=6.8Hz), 1.26 3H, d, J=6.0Hz), 3.79(6H, s), 6.88(1H, br, s). |

Note:
The production proportion of the (R)-compound and the (S)-compound was calculated from the NMR data.

REFERENCE EXAMPLE 4-(3)

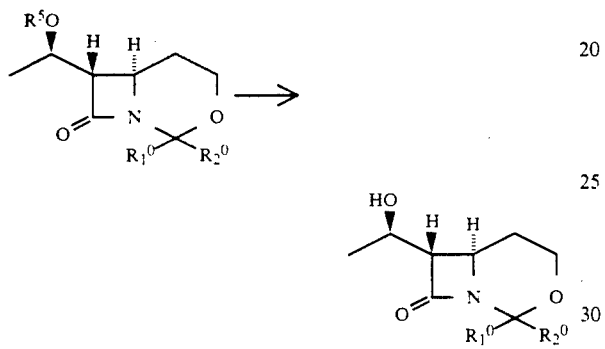

In the similar procedure to the one as described in Reference Example 3-(1), 3-(2), 4-(1) or 4-(2), there were obtained the compounds as shown in Table 4.

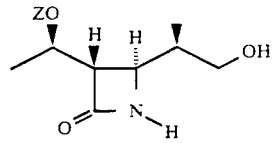

To a solution of (3S,4R)-4-(1-(R)-t-butyldimethyl-silyloxymethylethyl)-3-(1-(R)-benzyloxycarbonyloxyethyl)-1-di(p-anisyl)methyl-2-azetidinone (20 g) in dry dichloromethane (200 ml) were added 1,3-dimethoxybenzene (7.8 g) and boron trifluoride etherate (23 g) at 10°–20° C., and the resultant mixture was stirred at room temperature for 3 hours, followed by heating under reflux for 3–5 hours. The reaction mixture was cooled down to 10°–15° C., washed successively with brine (200 ml×2), 2.5% sodium bicarbonate (200 ml) and brine (200 ml) and dried over anhydrous sodium sulfate. Filtration and concentration of the filtrate in

TABLE 4

| | Starting material | | | | Reaction condition | | | | Objective compound |
|---|---|---|---|---|---|---|---|---|---|---|
| No. | R$^5$ | R$_1^0$ | R$_2^0$ | Amount | Catalyst | Solvent (ml) | Temp. (°C.) | Time (hr) | Ratio* (R/S) | Spectra data |
| 1 | Z | Me | Me | 18 (g) | 10% Pd/C (3.6 g) | EtOH (180) | 0–5 | 1 | 2.2 | NMR δ (CDCl$_3$) of (R)-compound: 1.11(3H, d, J=7.0Hz), 1.30(3H, |
| 2 | H | Me | Me | 7.5 (mg) | 10% Pd/C (7 mg) | EtOH (1) | room temp. | 3.5 | 1.5 | d, J=6.5Hz), 1.41(3H, s), 1.72 (3H, s), 3.04(1H, dd, J=2.0 and 6.0Hz). |
| 3 | H | Me | Me | 15 (mg) | PtO$_2$ (3 mg) | EtOH (1.5) | room temp. | 1.5 | 2.82 | NMR δ (CDCl$_3$) of (S)-compound: 1.30(3H, d, J= 6.5Hz), 1.41(3H, s), 1.72(3H, s), 2.81(1H, dd, J=1.5 and 5.5Hz). |
| 4 | Z | —(CH$_2$)$_5$— | | 190 (mg) | 10% Pd/C (38 mg) | EtOH (2) | room temp. | 1 | 1.72 | NMR δ (CDCl$_3$) of (R)-compound: 1.11(3H, d, J=7.2Hz), 1.28(3H, |
| 5 | H | —(CH$_2$)$_5$— | | 10 (mg) | PtO$_2$ (2 mg) | EtOH (1.5) | room temp. | 1.5 | 3.0 | d, J=6.5Hz), 3.01(1H, dd, J= 2.0 and 5.7Hz). NMR δ (CDCl$_3$) of (S)-compound: 0.90(3H, d, J=6.5Hz), 1.28 (3H, d, J=6.5Hz), 2.77(1H, dd, J=1.5 and 5.5Hz). |

Note:
*The production proportion of the (R)-compound and the (S)-compound was calculated from the NMR data.

REFERENCE EXAMPLE 5-(1)

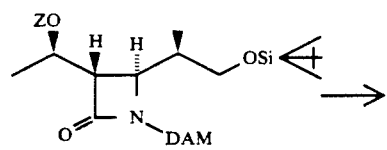

vacuo gave an oily residue which was purified by silica gel chromatography to yield (3S,4S)-4-(1-(R)-hydroxymethylethyl)-3-(1-(R)-benzyloxycarbonyloxyethyl)-2-azetidinone.

IR $\nu_{max}^{neat}$ (cm$^{-1}$): 3350, 1750, 1740, 1455, 1382, 1260, 1030.

NMR δ (CDCl$_3$): 0.95 (3H, d, J=7.0 Hz), 1.48 (3H, d, J=6.5 Hz), 3.14 (1H, dd, J=2 and 9 Hz), 3.55 (1H, d, J=2 Hz), 5.15 (2H, s), 6.05 (1H, br, s), 7.37 (5H, s).

REFERENCE EXAMPLE 5-(2)

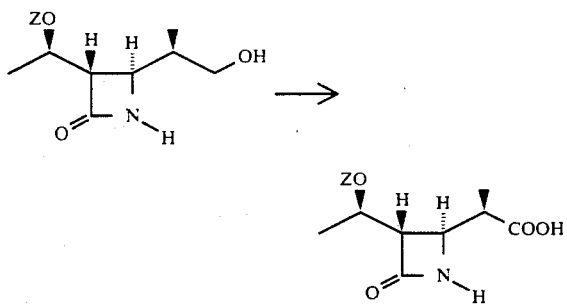

A solution of (3S,4S)-4-(1-(R)-hydroxymethylethyl)-3-(1-(R)-benzyloxycarbonyloxyethyl)-2-azetidinone (6.1 g) in acetone (60 ml) was treated with the Jones reagent, prepared from chromium trioxide (2.78 g), 98% sulfuric acid (4.4 g) and water (8.1 ml), at 10°–20° C. for 1 hour. The reaction mixture was quenched with isopropanol (0.5 ml) at 10°–20° C. for 15 minutes, diluted with ethyl acetate (122 ml) and washed with water (135 ml). The aqueous layer was separated from the organic layer and extracted with ethyl acetate (61 ml). The ethyl acetate extracts and the organic layer were combined together and extracted with 5% sodium bicarbonate (30 ml). The extract was washed with dichloromethane (60 ml) and acidified with 10% hydrochloric acid solution (20 ml) with ice-cooling. The acidic solution was extracted twice with dichloromethane (60 ml). The extracts were washed with brine and dried over anhydrous sodium sulfate. Filtration and concentration of the filtrate in vacuo gave (3S,4S)-4-(1-(R)-carboxyethyl)-3-(1-(R)-benzyloxycarbonyloxyethyl)-2-azetidinone.

IR $\nu_{max}^{neat}$ (cm$^{-1}$) 3270, 1740, 1460, 1385, 1270, 750.

NMR δ (CDCl$_3$): 1.19 (3H, d, J=7.0 Hz), 1.40 (3H, d, J=6.2 Hz), 2.67 (1H, m), 3.22 (1H, br, d, J=7.5 Hz), 3.84 (1H, br, d, J=5.5 Hz), 5.14 (2H, s), 6.57 (1H, br, s), 7.35 (5H, s), 7.63 (1H, br, s).

REFERENCE EXAMPLE 6-(1)

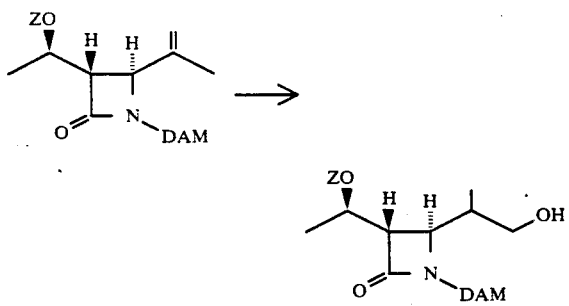

To a solution of sodium borohydride (0.32 g) in dry tetrahydrofuran (40 ml) was added dropwise boron trifluoride-etherate (1.81 g) at 10°–20° C. under nitrogen gas, and the resultant mixture was stirred for 1 hour. After addition of 1,5-octadiene (1.21 g) and stirring for 1 hour, a solution of (3S,4S)-4-(1-methylethenyl)-3-(1-(R)-benzyloxycarbonyloxyethyl)-1-di(p-anisyl)methyl-2-azetidinone (2.63 g) in dry tetrahydrofuran (10 ml) was dropwise added thereto at 20°–25° C. over a period of 1 hour, followed by stirring for 3 hours. The reaction mixture was quenched with water (7 ml) at 10°–30° C. for 1 hour. After addition of 4% sodium bicarbonate solution (5.3 ml), the mixture was heated at 40°–45° C., treated with 35% hydrogen peroxide solution (5.3 ml) at 40°–45° C. and cooled down to room temperature. Sodium sulfite (0.2 g) and toluene (6 ml) were added to the mixture, followed by stirring. The organic layer was separated and the aqueous layer was extracted with toluene (12 ml). The combined extracts were washed with brine and dried over anhydrous sodium sulfate. Filtration and concentration of the filtrate in vacuo gave an oily residue, which was purified by silica gel chromatography to yield (3S,4R) 4-(1-(S)-hydroxymethylethyl)-3-(1-(R)-benzyloxycarbonyloxyethyl)-1-di(p-anisyl)methyl-2-azetidinone (1.88 g) and the corresponding 4-(1-(R)-hydroxymethylethyl) compound (0.51 g).

IR $\nu_{max}^{neat}$ (cm$^{-1}$): 3450, 1745, 1615, 1515, 1460, 1385, 1260, 1180, 1035.

(S)-Compound:
NMR δ (CDCl$_3$): 0.73 (3H, d, J=6.8 Hz), 1.41 (3H, d, J=6.4 Hz), 2.93 (1H, dd, J=2.2 and 6 Hz), 3.73 (3H, s), 3.75 (3H, s), 5.11 (2H, s), 5.55 (1H, s), 7.37 (5H, s).

(R)-Compound:
NMR δ (CDCl$_3$): 0.89 (3H, d, J=6.8 Hz), 1.41 (3H, d, J=6.4 Hz), 3.17 (1H, dd, J=2.2 and 7.5 Hz), 3.73 (3H, s), 3.75 (3H, s), 5.16 (2H, s), 5.60 (1H, s), 7.37 (5H, s).

REFERENCE EXAMPLE 6-(2)

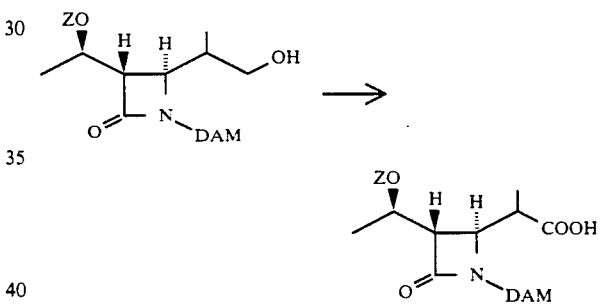

Following the procedure as described in Reference Example 5-(2) but replacing the starting material by (3S,4R)-4-(1-hydroxymethylethyl)-3-(1-(R)-benzyloxycarbonyloxyethyl)-1-di(p-anisyl)methyl-2-azetidinone, there was obtained (3S,4S)-4-(1-carboxyethyl)-3-(1-(R)-benzyloxycarbonyloxyethyl)-1-di(p-anisyl)methyl-2-azetidinone.

IR$\nu_{max}^{neat}$(cm$^{-1}$): 1740, 1608, 1510, 1250, 1170, 1023.

REFERENCE EXAMPLE 7

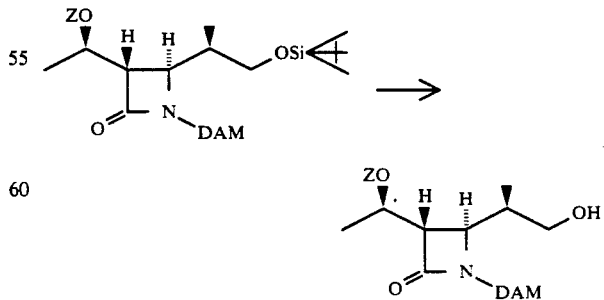

A solution of (3S,4R)-4-(1-(R)-t-butyldimethylsilyloxymethylethyl)-3-(1-(R)-benzyloxycarbonyloxyethyl)-1-di(p-anisyl)methyl-2-azetidinone (0.40 g) in methanol (40 ml) was treated with 6N hydrochloric acid (10 ml) with ice-cooling for 20 minutes. The reaction mixture was diluted with ethyl acetate (200 ml), washed with brine and dried over anhydrous sodium sulfate. Filtration and concentration of the filtrate in vacuo gave an oily residue, which was purified by silica gel chromatography to yield (3S,4R)- 4-(1-(R)-hydroxymethylethyl)-3-(1-(R)-benzyloxycarbonyloxyethyl)-1-di(p-anisyl)methyl-2-azetidinone.

IR and NMR spectra data of this product were identical to those of the (R)-compound obtained in Reference Example 6-(1).

REFERENCE EXAMPLE 8-(1)

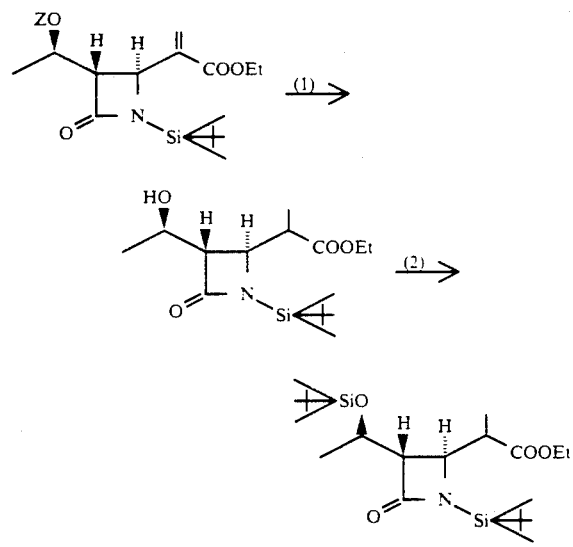

(1) A solution of (3S,4S)-4-(1-ethoxycarbonylethenyl)-3-(1-(R)-benzyloxycarbonyloxyethyl)-t-butyldimethylsilyl-2-azetidinone (14.6 g) in ethanol (139 ml) containing 0.01M phosphate buffer (pH, 5.7; 7 ml) was hydrogenated under hydrogen atmosphere in the presence of 10% Pd/C (2.92 g) at room temperature for 2 hours. The catalyst was collected by filtration and washed with ethyl acetate (100 ml). The filtrate and the washings were diluted with ethyl acetate (500 ml), washed with brine, dried over anhydrous sodium sulfate and evaporated in vacuo to give the crude product.

(2) The crude product as obtained above was dissolved in dry benzene (100 ml) and evaporated in vacuo to dryness. The residue was treated with t-butyl dimethylchlorosilane by the similar procedure to that as described in Example 14 to yield (3S,4S)-4-(1-ethoxycarbonylethyl)-3-(1-(R)-t-butyldimethylsilyloxyethyl)-1-t-butyldimethylsilyl-2-azetidinone.

IR $\nu_{max}^{neat}$ (cm$^{-1}$): 1745, 1460, 1365, 1320, 1250, 1185, 835, 772.

REFERENCE EXAMPLE 8-(2)

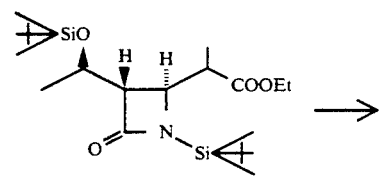

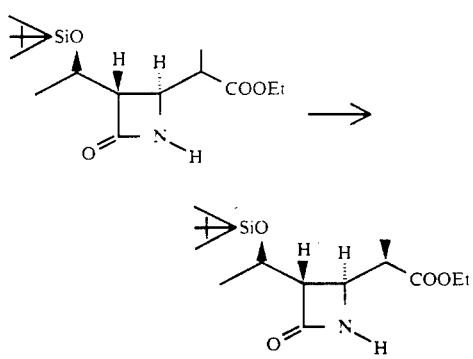

A solution of (3S,4S)-4-(1-ethoxycarbonylethyl)-3-(1-(R)-t-butyldimethylsilyloxyethyl)-1-t-butyldimethylsilyl-2-azetidinone (46.3 g) in dry tetrahydrofuran (60 ml) was treated with a 1M tetrahydrofuran solution of tetra-n-butylammonium fluoride (96 ml) at room temperature for 45 minutes. The reaction mixture was diluted with ethyl acetate (250 ml) and washed with brine (60 ml). The washing was extracted with ethyl acetate (50 ml). The extract and the ethyl acetate layer were combined together, washed with brine and dried over anhydrous sodium sulfate. Filtration and concentration of the filtrate in vacuo gave an oily residue, which was purified by silica gel chromatography to yield (3S,4S)-4-(1-ethoxycarbonylethyl)-3-(1-(R)-t-butyldimethylsilyloxyethyl)-2-azetidinone.

High performance liquid chromatography (HPLC) [Lichrosorb ® SI-60]eluting with 5% isopropanol/n-hexane (1 ml/min) indicated that this product was a mixture of the 4-(1-(R)-ethoxycarbonylethyl) compound and the corresponding (S)-compound in a weight ratio of 3.7 : 1. The above mixture was recrystallized twice from n-hexane to yield the product in a ratio of 10.3 : 1 (R : S).

IR $\nu_{max}^{neat}$ (cm$^{-1}$): 3250, 1750, 1465, 1378, 1250, 1100, 835, 775.

(R)-Compound:
NMR δ (CDCl$_3$): 0.08 (6H, s), 0.88 (9H, s), 1.17 (3H, d, J=6 Hz), 1.23 (3H, d, J =7 Hz), 1.28 (3H, t, J=7 Hz), 2.97 (1H, dd, J=2.2 and 4 Hz), 3.88 (1H, dd, J=2.2 and 6 Hz), 4.17 (2H, q, J=7 Hz).

(S)-Compound:
NMR δ (CDCl$_3$): 0.08 (6H, s), 0.88 (9H, s), 1.23 (3H, d, J=6 Hz), 1.24 (3H, d, J =7 Hz), 1.28 (3H, t, J=7 Hz), 2.76 (1H, m), 3.69 (1H, dd, J =2.2 and 10 Hz), 4.16 (2H, q, J=7 Hz).

REFERENCE EXAMPLE 9

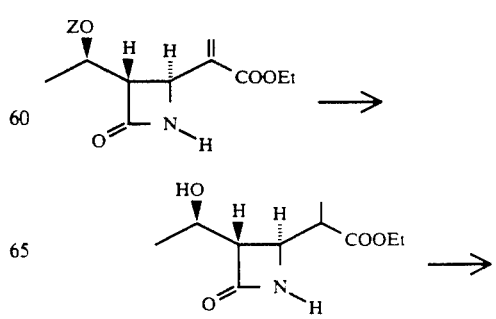

-continued

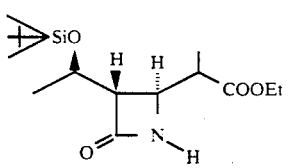

(1) A solution of (3S,4S)-4-(1-ethoxycarbonylethenyl)-3-(1-(R)-benzyloxycarbonyloxyethyl)-2-azetidinone (40.0 g) in ethanol (600 ml) was hydrogenated under hydrogen atmosphere in the presence of 10% Pd/C (20.0 g) at room temperature for 3 hours. The mixture was filtered, and the filtrate was evaporated in vacuo to give (3S,4S)-4-(1-ethoxycarbonylethyl)-3-(1-(R)-hydroxyethyl)-2-azetidinone as a yellowish oil.

NMR δ (CDCl$_3$): 1.20 (3H, d, J=7.0 Hz), 1.28 (3H, d, J=6.8 Hz), 1.29 (3H, t, J=7.0 Hz), 2.60 (1H, m), 3.78 (1H, dd, J=2.2 and 8.6 Hz), 4.14 (1H, m), 4.17 (2H, q, J=7.0 Hz), 6.71 (1H, br, s).

(2) Following the procedure as described in Example 4-(1) but replacing the starting material by the product as obtained in (1) above, there was obtained (3S,4S)-4-(1-ethoxycarbonylethyl)-3-(1-(R)-t-butyldimethylsilyloxyethyl)-2-azetidinone.

NMR spectra indicated that this product was a mixture of the 4-(1-(R)-ethoxycarbonylethyl) compound and the corresponding (S)-compound in a weight ratio of 1:4.3. IR and NMR spectra data of this product were identical to those as obtained in Reference Example 8-(2).

REFERENCE EXAMPLE 10-(1)

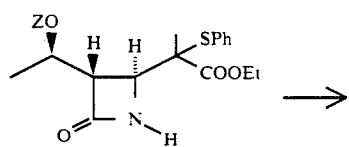

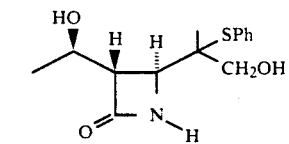

Calcium chloride (242 mg) and sodium borohydride (82 mg) were heated in dry tetrahydrofuran (10 ml) under reflux for 3.5 hours in nitrogen stream to give a calcium borohydride solution. A solution of (3S,4S)-4-(1-phenylthio-1-ethoxycarbonylethyl)-3-(1-(R)-benzyloxycarbonyloxyethyl)-2-azetidinone (250 mg) in dry tetrahydrofuran (5 ml) was added thereto, and the resultant mixture was stirred under reflux for 1.5 hours. After cooling, 1N hydrochloric acid was added thereto to decompose excess calcium borohydride. The reaction mixture was extracted with ethyl acetate (30 ml×3). The extracts were combined together, washed successively with 5% sodium bicarbonate and brine and dried over anhydrous magnesium sulfate. Filtration and concentration of the filtrate in vacuo gave an oily residue, which was purified by thin-layer chromatography [SiO$_2$; CHCl$_3$—MeOH (5:1)] to yield two epimers of (3S,4S)-4-(1-phenylthio-1-hydroxymethylethyl)-3-(1 (R) benzyloxycarbonyloxyethyl)-2-azetidinone (Compounds A and B).

Compound B:
NMR δ (CDCl$_3$): 1.14 (3H, s), 1.39 (3H, d, J=6.2 Hz), 3.37 (1H, dd, J=1.8 and 7.7 Hz), 3.55 (2H, AB$_q$, J=2.9 Hz), 3.83 (1H, d, J=2.2 Hz), 4.15 (1H, m), 6.56 (1H, bs), 7.37 and 7.49 (5H, m).

Compound A:
NMR δ (CDCl$_3$): 1.16 (3H, s), 1.28 (3H, d, J=7.0 Hz), 3.12 (1H, dd, J=1.8 and 7.5 Hz), 3.60 (2H, s), 3.65 (1H, d, J =2.0 Hz), 4.07 (1H, m), 6.61 (1H, bs), 7.37 (5H, m).

REFERENCE EXAMPLE 10-(2)

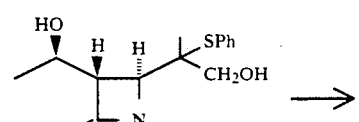

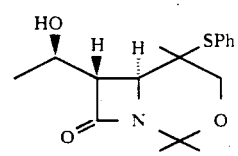

Following the procedure as described in Example but replacing the starting material by (3S,4S)-4-(1-phenylethyl-1-hydroxymethylethyl)-3-(1-(R)-benzyloxycarbonyloxyethyl)-2-azetidinone (Compound B), there was obtained (6S,7S)-8-oxo-2,2-dimethyl-5-methyl-5-phenylthio-7-(1-(R)-hydroxyethyl)-3-oxa-1-azabicyclo[4,2,0]octane.

NMR δ (CDCl$_3$): 1.23 (6H, s), 1.31 (3H, d, J=6.4 Hz), 1.62 (3H, s), 2.02 (1H, br, s), 3.04 (1H, dd, J=1.9 and 5.8 Hz), 3.43 (1H, d, J=11.9 Hz), 3.56 (1H, d, J=1.5 Hz), 3.73 (1H, d, J=12.1 Hz), 4.06 (1H, m), 7.32 and 7.40 (5H, m).

REFERENCE EXAMPLE 10-(3)

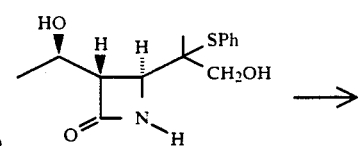

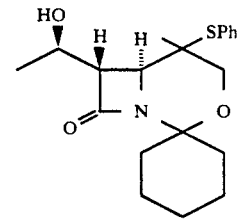

Following the procedure as described in Example 10-(2) but replacing 2,2-dimethoxypropane by 1,1-dimethoxycyclohexane, there was obtained (6S,7S)-spirocyclohexane-2,2-(8-oxo-5-methyl-5-phenylthio-7-(1-(R)-hydroxyethyl)-3-oxa-1-azabicyclo[4.2.0]octane].

IR $v_{max}^{Nujol}$ (cm$^{-1}$): 3450, 1755, 1208, 1170, 1060, 750.

REFERENCE EXAMPLE 11

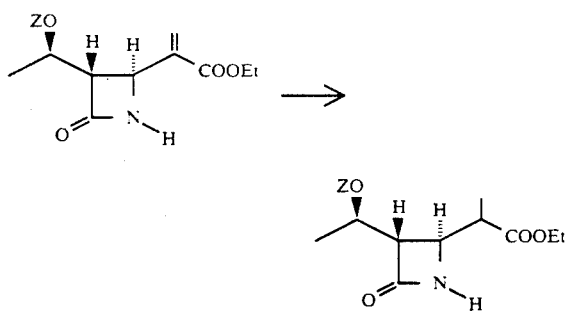

A solution of (3S,4S)-4-(1-ethoxycarbonylethenyl)-3-(1-(R)-benzyloxycarbonyloxyethyl)-2-azetidinone (1.04 g) in isopropanol (20 ml) and water (10 ml) was treated with sodium borohydride (230 mg) in the presence of nickel chloride (40 mg) at 0°–5° C. for 15 minutes. After stirring at room temperature for additional 1 hour, the reaction mixture was diluted with ethyl acetate (300 ml), washed with brine and dried over anhydrous sodium sulfate. Filtration and concentration of the filtrate in vacuo gave an oily residue, which was purified by silica gel chromatography to yield (3S,4S)-4-(1-ethoxycarbonylethyl)-3-(1-(R)-benzyloxycarbonyloxyethyl)-2-azetidinone.

NMR δ (CDCl$_3$): 1.38 (3H, d, J=6 Hz), 2.90 (1H, dd, J=2 and 8 Hz), 3.59 (1H, dd, J=2 and 9 Hz), 4.09 (2H, q, J=7 Hz), 5.08 (2H, s), 6.30 (1H, br, s), 7.31 (5H, s).

The weight proportion of the 4-(1-(R)-ethoxycarbonylethyl) compound and the corresponding (S)-compound in this product was confirmed to be 1 : 4 by HPLC (measured at the same condition as described in Reference Example 8-(2)) and NMR spectra.

The above (S)-compound was preferentially obtained by the similar procedure to that as described above, when the additives and the solvents as shown in Table 5 below were used.

TABLE 5

| Reducing agent | Additive | Solvent | Ratio* (S/R) |
|---|---|---|---|
| NaBH$_4$ | NiCl$_2$ | MeOH-water (2:1) | 1.28 |
| NaBH$_4$ | NiCl$_2$ | THF-MeOH (4:1) | 3.33 |
| NaBH$_4$ | CoCl$_2$ | MeOH-water (2:1) | 1.41 |
| NaBH$_4$ | CoCl$_2$ | Isopropanol | only (S)-compound |
| NaBH$_4$ | CuCl$_2$ | EtOH | 1.5 |
| NaBH$_4$ | CuCl$_2$ | Isopropanol-water (4:1) | 2.0 |
| NaBH$_4$ | CuCl$_2$ | Isopropanol | 4.0 |
| NaBH$_4$ | CuCl$_2$ | MeOH | 2.0 |

Note:
*The production proportion of the (R)-compound and the (S)-compound was calculated from the NMR data.

REFERENCE EXAMPLE 12

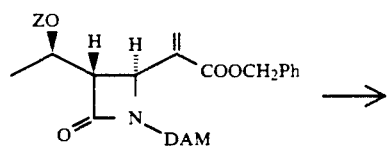

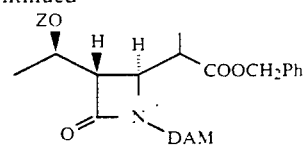

A solution of (3S,4S)-4-(1-benzyloxycarbonylethenyl)-3-(1-(R)-benzyloxycarbonyloxyethyl)-1-di(p-anisyl)methyl-2-azetidinone (63 mg) in methanol (1.5 ml) was treated with sodium borohydride (7.7 mg) in the presence of nickel chloride (1.3 mg) at 0°–5° C. for 15 minutes. After stirring at room temperature for an additional 1 hour, the reaction mixture was diluted with ethyl acetate (30 ml), washed with brine and dried over anhydrous sodium sulfate. Filtration and concentration of the filtrate in vacuo gave an oily residue, which was purified by thin-layer chromatography (SiO$_2$) to yield (3S,4S)-4-(1-benzyloxycarbonylethyl)-3-(1-(R)-benzyloxycarbonyloxyethyl)-1-di(p-anisyl)methyl-2-azetidinone.

The production proportion of the 4-(1-(R)-benzyloxycarbonylethyl) compound and the corresponding (S)-compound in this product was confirmed to be 4:1 by the NMR data.

IR $\nu_{max}^{neat}$ (cm$^{-1}$): 1745, 1610, 1585, 1510, 1455, 1382, 1245, 1175, 1025.

(R)-Compound:
NMR δ (CDCl$_3$): 1.06 (3H, d, J=7.0 Hz), 1.38 (3H, d, J=6.4 Hz), 3.35 (1H, dd, J=2.3 and 6.7 Hz), 3.70 (3H, s), 3.73 (3H, s), 5.15 (2H, s), 5.49 (1H, s), 7.36 (5H, s).

(S)-Compound:
NMR δ (CDCl$_3$): 1.06 (3H, d, J=7.0 Hz), 1.34 (3H, d, J=6.2 Hz), 3.04 (1H, dd, J=2.2 and 7.0 Hz), 3.71 (3H, s), 3.73 (3H, s), 5.15 (2H, s), 5.49 (1H, s), 7.32 (5H, s).

Following the above procedure, the (R)-compound was preferentially obtained by using the additives as shown in Table 6 instead of nickel chloride.

TABLE 6

| Additive | Solvent | Ratio* (R/S) |
|---|---|---|
| CoCl$_2$ | MeOH | 2.0 |
| CuCl$_2$ | MeOH | 2.2 |

Note:
*The production proportion of the (R)-compound and the (S)-compound was calculated from the NMR data.

REFERENCE EXAMPLE 13

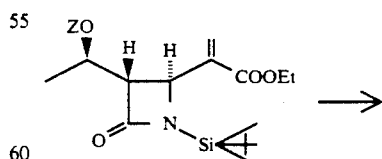

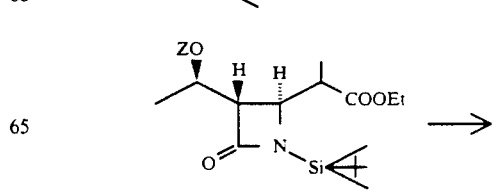

-continued

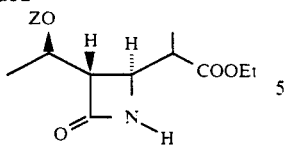

Following the procedure as described in Reference Examples 12 and 8-(2) but using (3S,4S)-4-[1l-ethoxycarbonylethenyl)-3(1-(R)-benzyloxycarbonyloxyethyl)-1-t-butyldimethylsilyl-2-azetidinone as the starting material, there was obtained (3S,4S)-4-(1-ethoxycarbonylethyl)-3-(1-(R)-benzyloxycarbonyloxyethyl)-2-azetidinone.

The weight proportion of the 4-(1-(R)-ethoxycarbonylethyl) compound and the corresponding (S)-compound in this product was confirmed to be 3.6:1 by the NMR data.

What is claimed is:
1. A compound of the formula

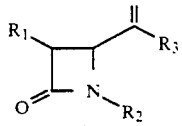

wherein $R_1$ is a hydrogen atom, a lower alkyl group or a 1-hydroxy(lower)alkyl group wherein the hydroxyl group is optionally protected, $R_2$ is a hydrogen atom or a protective group for the nitrogen atom and $R_3$ is a halomethyl or a formyl group.

* * * * *